(12) United States Patent
Ringold

(10) Patent No.: US 8,940,869 B2
(45) Date of Patent: Jan. 27, 2015

(54) METHOD AND SYSTEM FOR DETECTING AND DIFFERENTIATING CANCER AND SEPSIS IN MAMMALS USING BIOMARKERS

(71) Applicant: Veterinary Diagnostics Institute, Inc., Simi Valley, CA (US)

(72) Inventor: Randy Ringold, West Hills, CA (US)

(73) Assignee: Veterinary Diagnostics Institute, Inc., Simi Valley, CA (US)

( * ) Notice: Subject to any disclaimer, the term of this patent is extended or adjusted under 35 U.S.C. 154(b) by 41 days.

(21) Appl. No.: 13/672,677

(22) Filed: Nov. 8, 2012

(65) Prior Publication Data

US 2014/0127731 A1    May 8, 2014

(51) Int. Cl.
*C07K 14/58*    (2006.01)

(52) U.S. Cl.
USPC ........................................................ 530/350

(58) Field of Classification Search
CPC ............................ C07K 14/4737; C07K 14/58
USPC ........................................................ 530/350
See application file for complete search history.

(56) References Cited

U.S. PATENT DOCUMENTS

2005/0148029 A1    7/2005    Buechler et al.

FOREIGN PATENT DOCUMENTS

EP    2 060 920    5/2009

OTHER PUBLICATIONS

Declue et al. Journal of Veterinary Internal Medicine vol. 25 No. 3 May 2011 pp. 453-459.
Constance Gebhardt et al. Journal of Veterinary Emergency and Critical Care, vol. 19 No. 5 Oct. 1, 2009 pp. 450-458.

*Primary Examiner* — Karen Cochrane Carlson
(74) *Attorney, Agent, or Firm* — Karim Lagobi

(57) ABSTRACT

The invention provides a method and system for developing and using diagnoses of cancer and sepsis in canine subjects using Thymidine kinase (TK), c-reactive protein (CRP), and C-type natriuretic peptide (CNP) as biomarkers. The level of each biomarker may be measured and an index may be computed using a two- or a three-biomarker method. The invention provides a predefined scale for the index where each range of the index matches a health condition. The latter allows a practitioner, through computing an index value of a patient, to determine the health status of the patient by comparing the index value to the predefined scale.

2 Claims, 14 Drawing Sheets

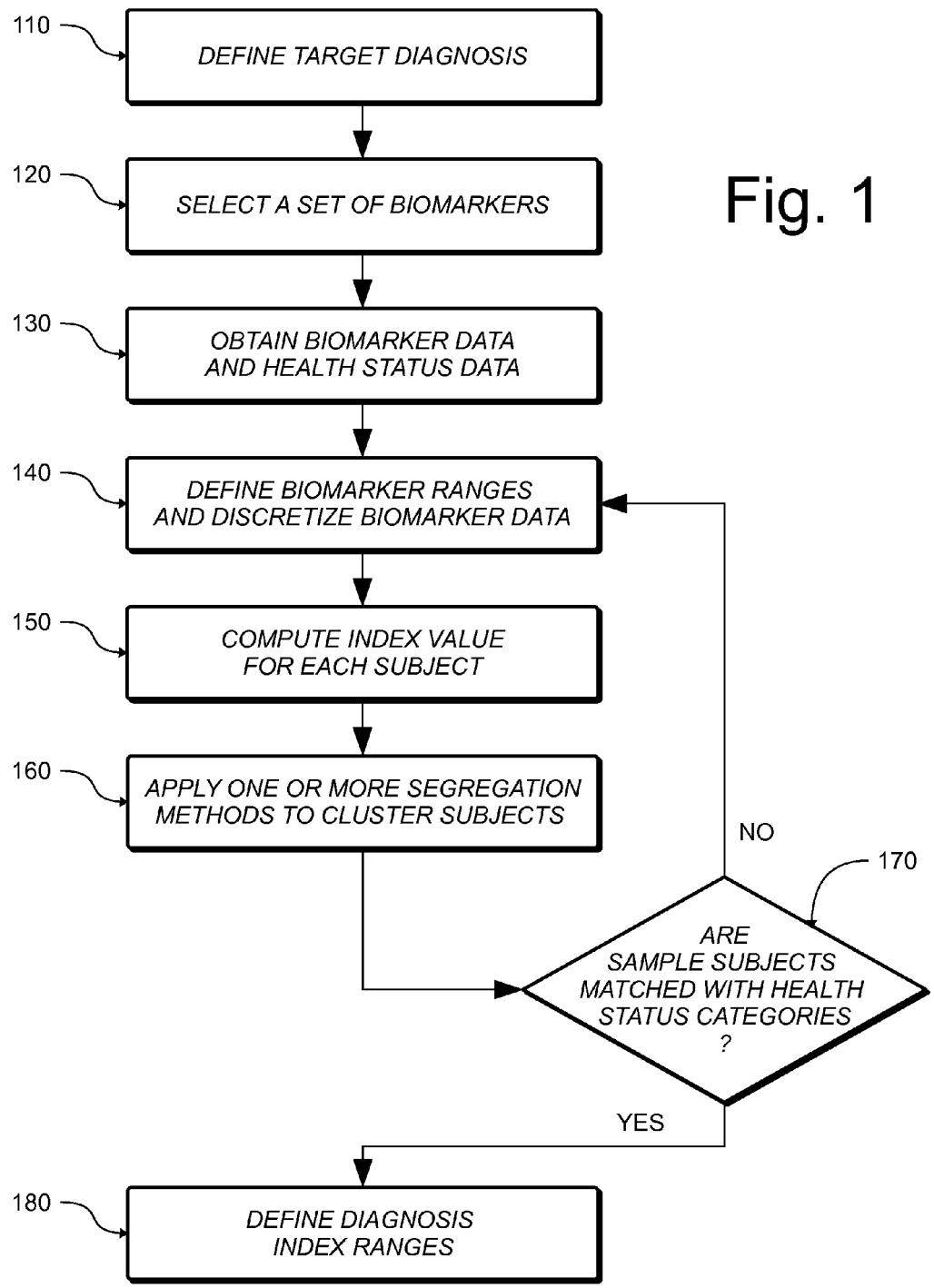

Fig. 5
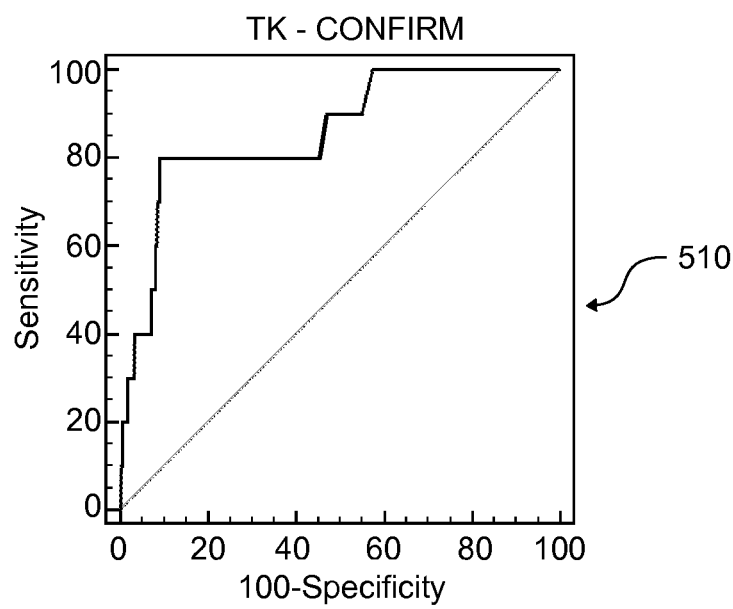
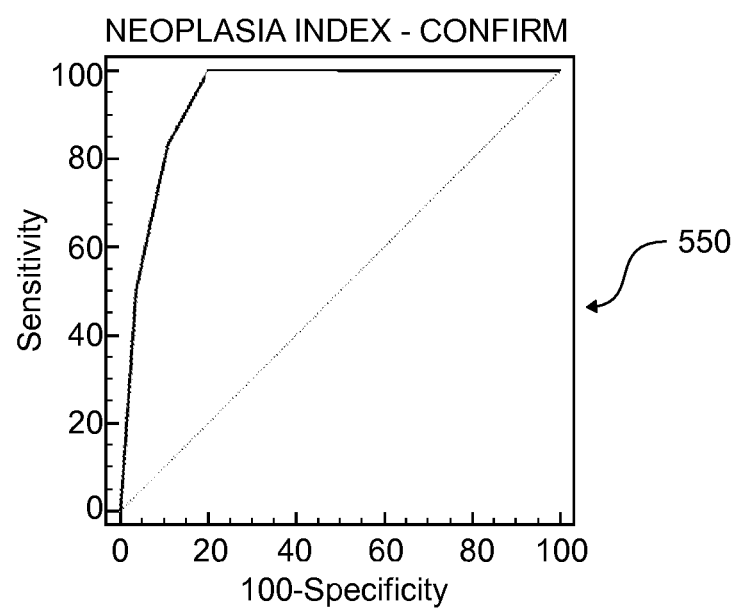

Fig. 6
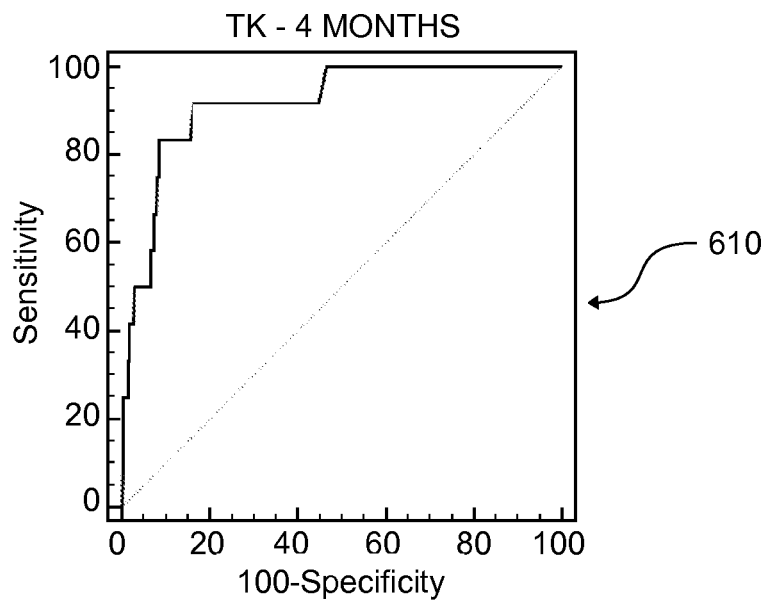
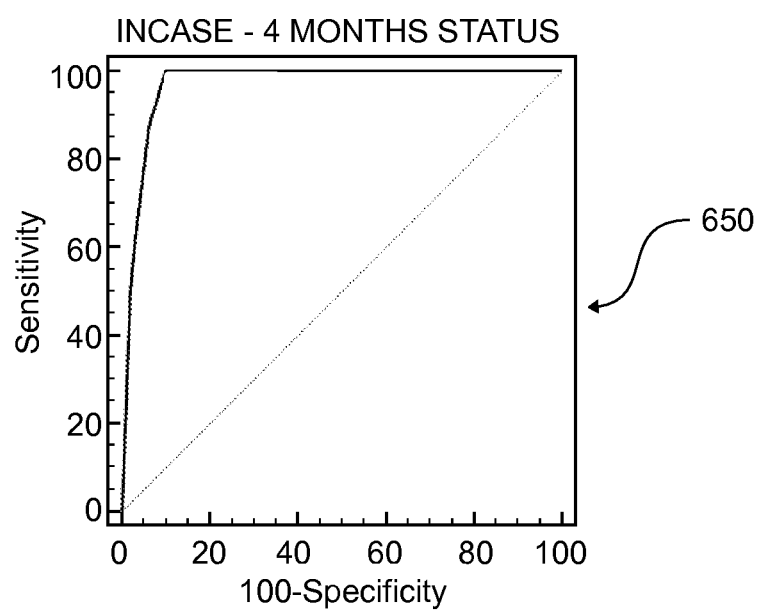

Fig. 7
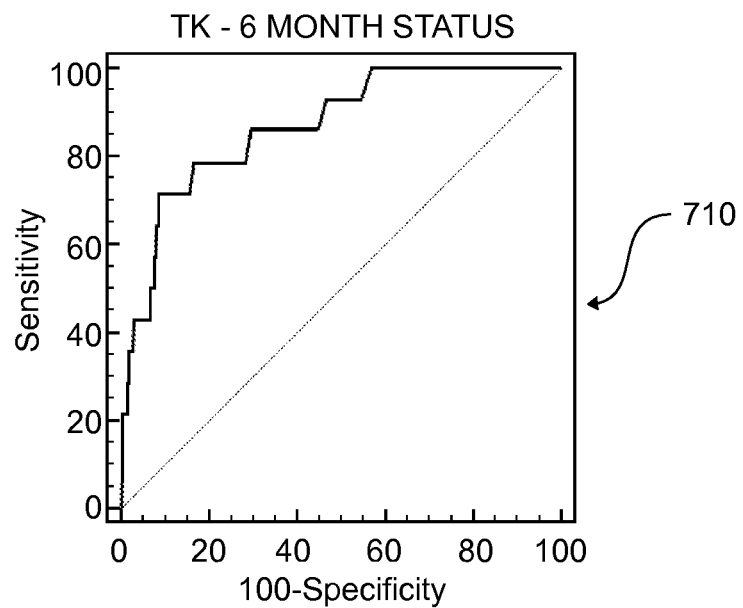
TK - 6 MONTH STATUS — 710
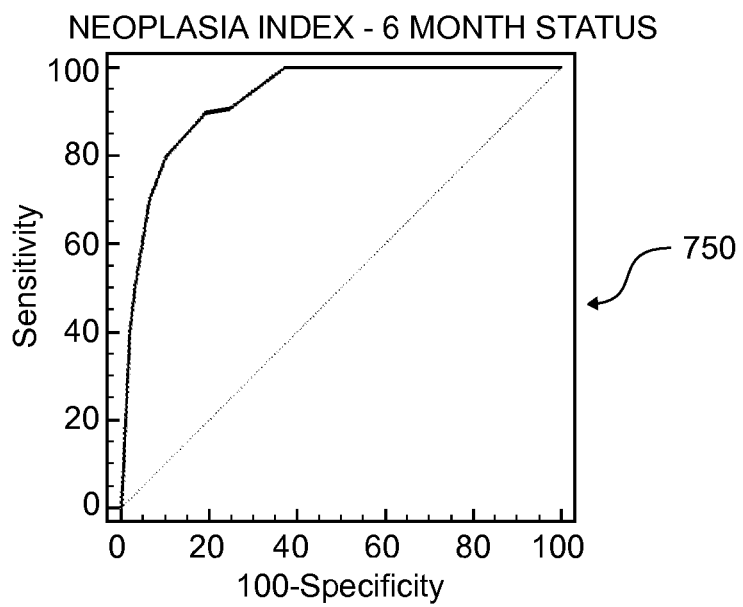
NEOPLASIA INDEX - 6 MONTH STATUS — 750

Fig. 9
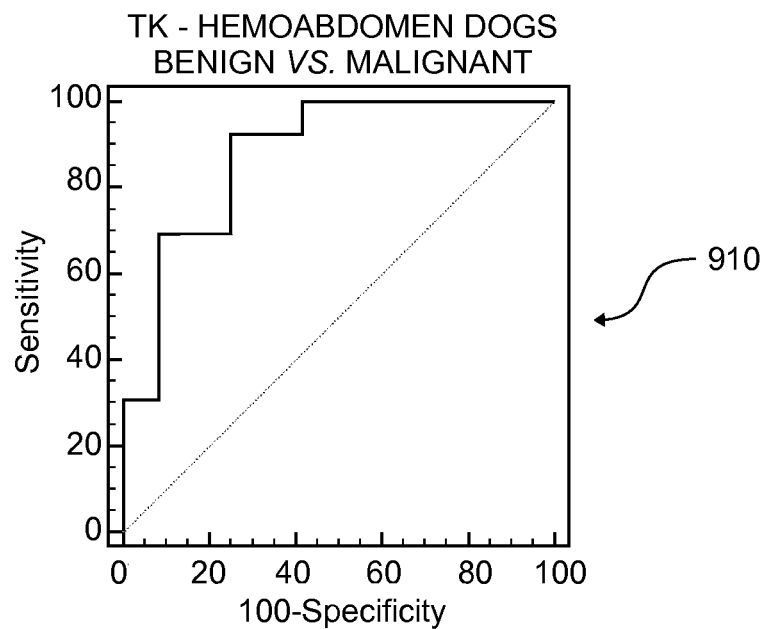
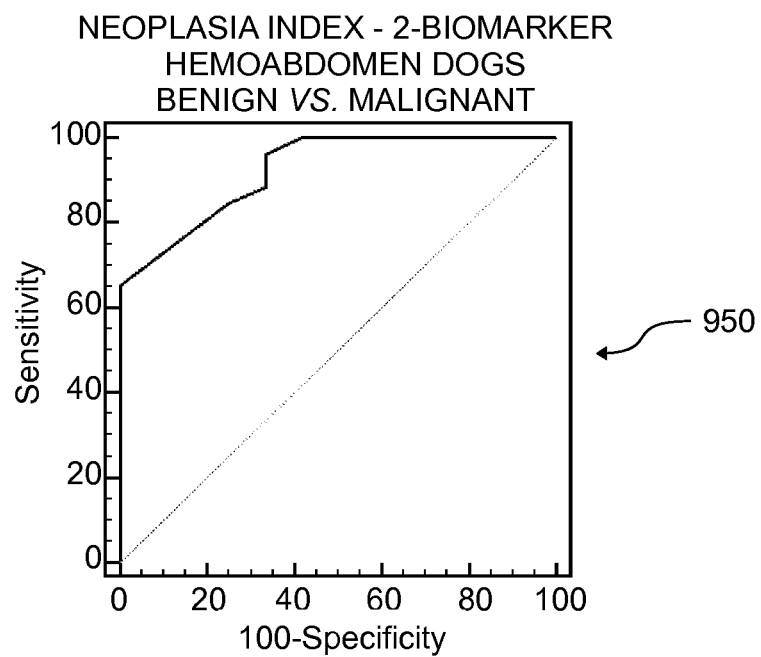

Fig. 10
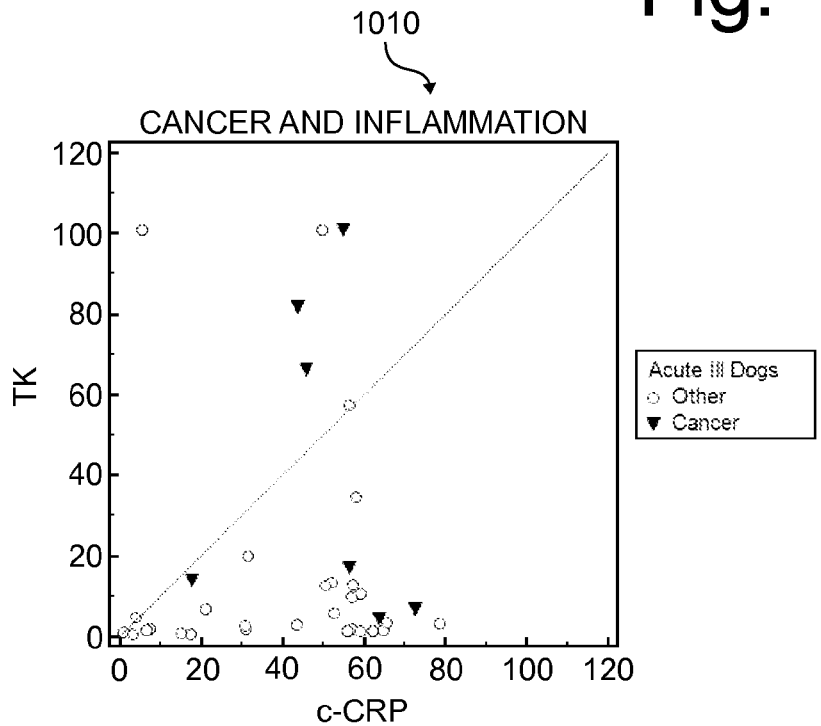
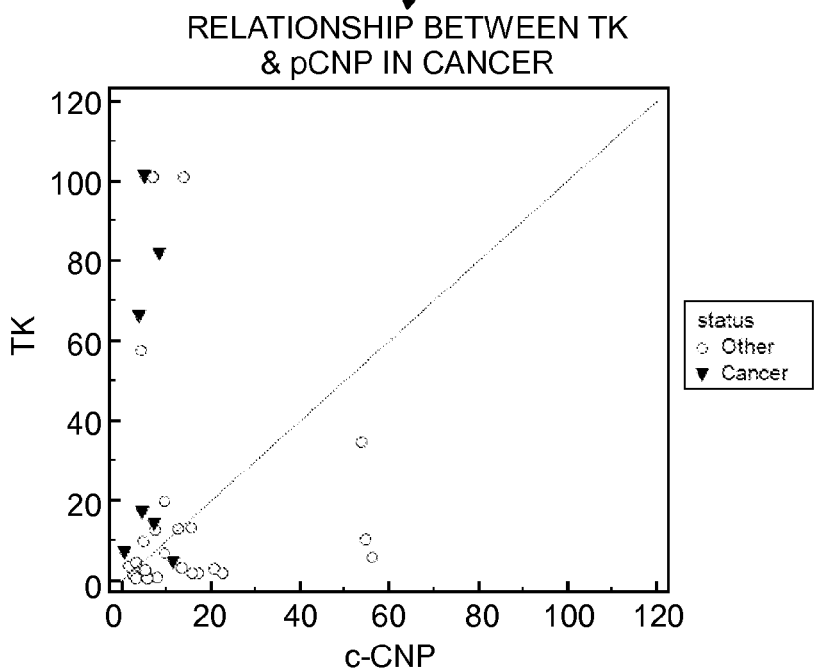

Fig. 13
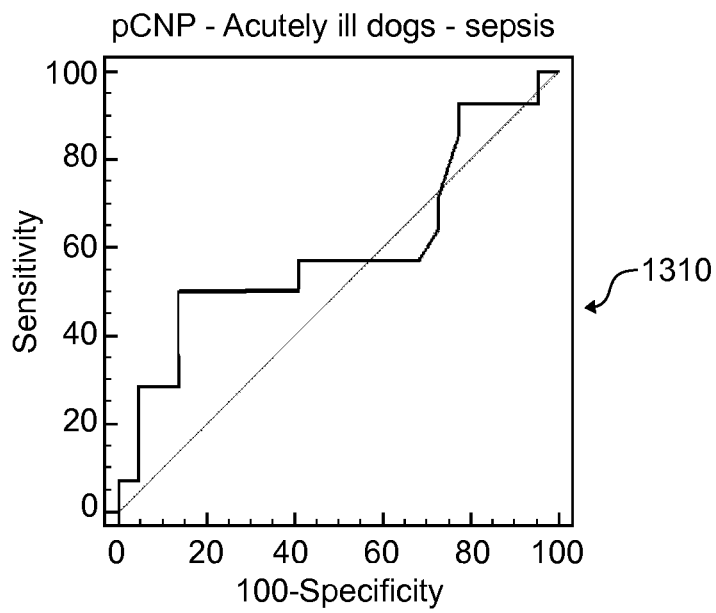
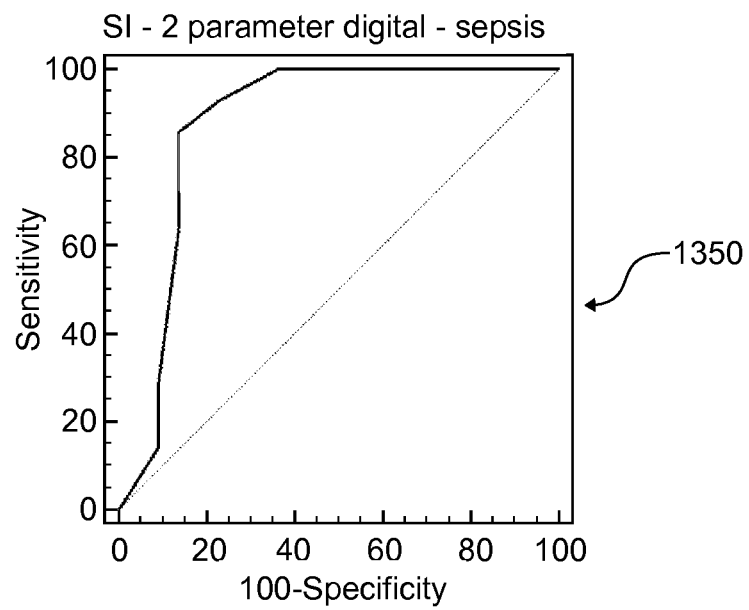

US 8,940,869 B2

METHOD AND SYSTEM FOR DETECTING AND DIFFERENTIATING CANCER AND SEPSIS IN MAMMALS USING BIOMARKERS

FIELD OF THE INVENTION

The invention relates to detecting disease in animals and humans; and particularly the invention provides a method and system for constructing a diagnosis for cancer and sepsis conditions in canines using a plurality of biomarkers, and further using the diagnosis to differentiate between cancer and sepsis affections regardless of the similarity in the apparent symptoms, and detect the propensity of a subject to develop cancer.

BACKGROUND OF THE INVENTION

The level of biomarkers in body fluids is used in the process of detecting numerous health affections. Measuring the level of one or more specific biomarkers in the blood is typically a fast and relatively inexpensive means for diagnosing a disease or leading to the diagnosis thereof before prescribing other (more expensive and/or time consuming) tests such as radiological, cytological, histological and immunological tests etc.

However, many challenges face a medical (or veterinary) practitioner in selecting a panel of biomarkers to be tested for any specific case, and then in interpreting the results of the measured level of each biomarker in view of the symptoms the patient is exhibiting. The symptoms are generally only broad indicators of any particular disease, since some diseases, such as infection-related diseases, trigger symptoms in a patient at the onset of the disease or shortly thereafter, while other diseases, such as many types of cancer, trigger symptoms a considerable time after a tumor starts to develop. Diagnosing the underlying disease often requires testing for a panel of biomarkers, where some tests may be conducted to confirm a suspicion of a disease, while other tests may be conducted to rule out one or more other diseases.

Along with the challenge of choosing the panel of biomarkers for testing, there is the challenge of interpreting the test results. Some biomarkers are proven to be tightly correlated with the presence of a certain disease, while other biomarkers provide only a probability level a patient has a particular disease. For example, in humans sustained hyperglycemia is a good indicator of diabetes, while, for example, in dogs an increased level of thymidine kinase above a given threshold is an indicator of Hemangiosarcoma, which should be confirmed through histology.

Moreover, screening, diagnosing and/or monitoring a disease may involve any number of tests. According to existing methods and systems, when using biomarkers the broader are the symptoms, the more tests are carried out. A practitioner uses his/her own experience to interpret the test results when using biomarkers to detect a disease, to follow the progression of a disease and/or to monitor the result of a treatment. The latter introduces a level of subjectivity in diagnosing test results, which may cause discrepancies between interpretations by the same person over time, among practitioners and even among entire health institutions.

Therefore, there is a need for a method and system for selecting a set of biomarkers and developing a method of use for detecting one or more target diseases and differentiating between the diseases to help a practitioner interpret the test results and potentially reveal the underlying affection or the propensity of a patient to develop a given disease.

SUMMARY OF THE INVENTION

The invention provides a method and system for constructing and using a diagnosis that reveals whether in a canine patient is affected by cancer or sepsis using a plurality of biomarkers, and further using the diagnosis to differentiate between the underlying health affections regardless of the commonality of symptoms.

Constructing a diagnosis following the invention involves selecting a set of biomarkers known for their relation with cancer and sepsis, and measuring the level of the biomarkers in a group of subjects. The invention teaches how to compute a numerical value, i.e. an index, using the biomarker levels, then define ranges of the index on a scale, where each range may be matched with a subgroup of subjects segregated on the basis of their health status. Provided the latter method of segregation of subjects by health status, a practitioner may subsequently utilize the index scale to diagnose a health affection in a patient by measuring the level of the biomarkers in the patient, then computing an index value for the patient and matching the value to the predefined index scale to determine whether the patient is likely affected by cancer or sepsis.

A system according to the invention may be implemented as a computer program configured to receive input data (e.g., biomarker data and health status data etc.), and determine ranges for a particular diagnosis. The computer system may also receive the input for a particular patient, compute the index value and output the result of the diagnosis. The system may stand alone or be embedded in any diagnosis machine.

Currently, practitioners are faced with the difficulty of interpreting the results of biomarker data, particularly when comparing the progress of a disease, such as while monitoring a subject with a particular propensity of having a disease, or monitoring the health progress of patients following a treatment. The invention provides the latter practitioners tools for diagnosing an underlying health affection and monitoring the progress of a disease using numerical indicators for any particular situation.

The invention teaches using a two-biomarker neoplasia index to detect the occurrence of cancer in canine subjects. Using thymidine kinase and c-reactive protein as biomarkers, the invention provides a means to detect whether a patient has a high probability of having cancer. The rate of success of the method to detect the health status of subjects is dramatically improved using a three-biomarker neoplasia index. The three-biomarker method uses thymidine kinase, c-reactive protein and C-type Natriuretic Peptide.

The invention provides means to detect and differentiate between subjects having cancer versus sepsis subjects or normal subjects. The latter method of detection may also use a two-biomarker or a three-biomarker index-based method according to the invention. The biomarkers in question are also, thymidine kinase and c-reactive protein and C-type Natriuretic Peptide. The invention teaches how to detect sepsis and/or differentiate between normal subjects and subjects affected with cancer subjects, on one hand, and subjects affected with sepsis, on the other hand, by selecting appropriate ranges of the index and the appropriate ranges of each biomarker.

DESCRIPTION OF THE DRAWINGS

FIG. 1 is a flowchart diagram representing steps involved in developing a method for detecting and/or differentiating one or more target diseases, in accordance with an embodiment of the invention.

FIG. 5 shows plots of the Receiver Operating Characteristic (ROC) curves Sensitivity vs. one hundred (100) minus Specificity using TK alone and the two-biomarker implementation of the invention following confirmation of cancer in a subset of subjects.

FIG. 6 shows plots of the ROC curves Sensitivity vs. one hundred (100) minus Specificity using TK alone and the two-biomarker implementation of the invention at four (4) months from the initial test.

FIG. 7 shows plots of the ROC curves Sensitivity vs. one hundred (100) minus Specificity using TK alone and the two-biomarker implementation of the invention at six (6) months from the initial test.

FIG. 9 shows plots of the Receiver Operating Characteristic (ROC) curves Sensitivity vs. one hundred (100) minus Specificity using TK alone and the two-biomarker implementation of the invention while considering malignant cancer vs. benign cancer.

FIG. 10 shows scatter plots representing TK vs. c-CRP data and TK vs. c-CNP data in a group of patients in which a subgroup was diagnosed with cancer.

FIG. 13 shows plots of the Receiver Operating Characteristic (ROC) curves Sensitivity vs. one hundred (100) minus Specificity results of using CNP data alone and using the two-biomarker (i.e., CNP and CPR) method while considering subjects with sepsis versus subjects diagnosed with other affections.

DETAILED DESCRIPTION OF THE INVENTION

Figure 2A:
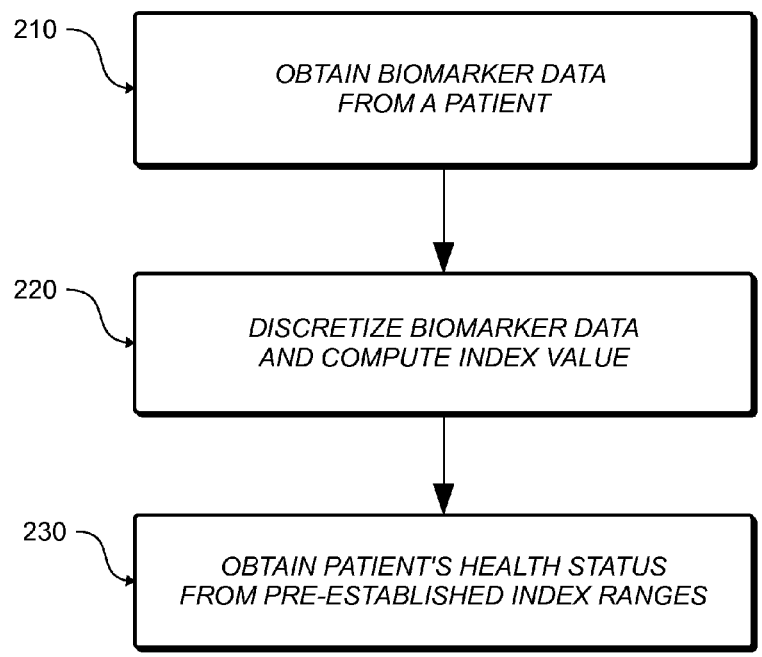
FIG. 2A is a flowchart of method steps involved in using a set of biomarkers in a diagnosis of one or more health statuses, in accordance with an implementation of the invention.

The invention provides a method and system for detecting disease in animals and humans. The invention provides a method and system for developing and using a diagnosis targeting a particular one or more health conditions using a plurality of biomarkers, and further using the diagnosis to differentiate between several affections that may trigger similar health symptoms in a patient. Furthermore, the method and system according to the invention may be used to determine the propensity for an individual to develop a disease (e.g., one or more types of cancer), providing a practitioner the means for detecting a disease before the symptoms are visible and/or monitoring a disease post treatment.

The disclosure presents a case, in a subject presenting general inflammation symptoms, of diagnosing whether the underlying affection is sepsis or cancer using two or three biomarkers.

In the following description, numerous specific details are set forth to provide a more thorough description of the invention. It will be apparent, however, to one skilled in the pertinent art, that the invention may be practiced without these specific details. In other instances, well known features have not been described in detail so as not to obscure the invention. The claims following this description are what define the metes and bounds of the invention.

Portions of the methods and systems disclosed in the present disclosure have been disclosed in co-pending patent application Ser. No. 13/672,649 and co-pending patent application Ser. No. 13/672,687.

Terminology

Throughout the description, the terms individual, subject or patient may refer to an animal subject or a person whose biological data are used to develop and/or use an implementation of the invention. The subject may be normal (or disease-free) or showing any level of symptoms.

The term biomarker refers to any indicator in any body part (e.g., bodily fluid or tissue) that may be collected and the presence of which measured through any of its manifestations such as enzymatic activity, mass, concentration, cell count, cell shrinkage/shape, deoxyribonucleic acid (DNA) and/or ribonucleic acid (RNA) genetic level of expression or any aspect of the biochemical or the physiological markers that may be related to one or more health conditions. Moreover, for the purpose of designing health status indices (see below) a biomarker data may be any related data that may be considered for diagnosing a disease (or the probability of occurrence thereof) such as age, sex, any biometric data, genetic history (e.g., parent's health status or presence of any affection in the family) or any other data that may contribute to the diagnosis of a disease.

The term "index" is used throughout the disclosure to refer to a dependent variable that is calculated using two or more data inputs such as the level of a biomarker in the blood stream. A "neoplasia index" refers to an index that is computed with the goal of classifying subjects into groups based on cancer status. For example, a subject that may be apparently healthy (e.g., showing no signs of cancer), diagnosed with a malignant or a benign cancer or in any health status with regard to cancer, would have an neoplasia index value that reflects the health status, in accordance with embodiments of the invention.

A "sepsis index", like the "neoplasia index" is calculated value on the basis of two or more biomarker levels, and may be mapped to the status of a subject with regard to sepsis affection, or a stage thereof.

Throughout the disclosure, the use of the name "C-reactive protein" and its abbreviation "CRP" in canine subjects refers to the specific family of canine C-reactive protein which may be specifically abbreviated as "c-CRP".

The term "user" may be used to refer to a person, machine or a computer program acting as or on behalf of a person.

General Concept of the Invention

The main concept of the invention is that by selecting a set of biomarkers and measuring their levels in an animal or a human subject, it is possible to compute a numerical value, i.e. an index, using those levels, and to compare the index value to a predefined scale that characterizes the health status of the subject using index ranges. The scale may define two or more ranges of the index values, wherein each range indicates a level of one or more diseases. For example, in a subject showing general symptoms of inflammation, a predefined scale may define two or more ranges that may indicate the presence of cancer, an infection, both cancer and infection or other diseases.

The invention teaches developing any particular diagnosis by selecting a set of biomarkers, then measuring the level of each biomarker from each individual of a sample group of subjects. In addition, other diagnoses (e.g., cytological, histological and physiological tests, physical examination etc.) are carried out on the subjects to accurately establish the health status of each subject.

According to embodiments of the invention, the biomarkers data serve to compute the index values, while the health status data serve to define two or more health status categories (e.g., healthy, cancer, benign tumor, infection etc.). Ranges of index values are then defined providing efficient segregation of subjects into the two or more health status categories.

Subsequently, to provide a diagnosis to a patient, a set of biomarkers according to a particular diagnosis is collected and measured, then an index value is computed using the test data, and the index value is compared to the predefined index scale to match a health status category, which reveals the patient's health status.

FIG. 1 is a flowchart diagram representing steps involved in developing a method for detecting and/or differentiating one or more target diseases, in accordance with an embodiment of the invention. Step 110 represents defining a target diagnosis. A typical target diagnosis involves defining a disease (e.g., Infection, any type of Cancer etc.) or two or more diseases that may or may not display common symptoms. Any prior knowledge with regard to the target disease(s) may be considered, thus, the symptoms that accompany the disease, the severity of the symptoms, the speed at which the symptoms develop and any other aspect of the disease profile may be considered to define the target diagnosis.

Step 120 represents selecting a set of biomarkers for use in the diagnosis. Selecting a set of biomarkers may be based on previous knowledge of a correlation (be it positive or negative) between the level of a given biomarkers and the presence (or absence) of the one or more target diseases. For example, thymidine kinase may be used as a biomarker to detect any type of cancer since thymidine kinase is typically present in the cells undergoing cell division, which is the case of cancerous cells.

Step 130 represents collecting data from a group of subjects. The group of subjects may be a sample of subjects comprising normal subjects (i.e. healthy) showing none of the symptoms defined in Step 110, and affected subjects showing any level of severity of those symptoms. Bodily fluids, tissue or any other body sample may be appropriately collected in order to measure the level of each biomarker of the set of biomarkers defined at step 120.

In addition, the subjects undergo a plurality of tests, such as histological, radiological tests or any other test designed to establish the presence or absence of the target disease(s). Other tests may be conducted on each subject to either further confirm the disease or rule out other diseases that may share common symptoms.

Moreover, other non-disease related data may also be considered. The latter data comprise age, sex, any biometric data, genetic history (e.g., parent's health status or presence of any affection in the family) or any other data that may contribute to the diagnosis of a disease.

The outcome of step 130 is a set of data points that characterizes each subject individual data and its level of each biomarker in the set of data, and a health status that establishes whether each subject is a non-carrier or a carrier of one or more diseases and eventually the stage (or severity) of each disease. For example, when considering cancer, a subject may be classified as non-carrier of cancer, having a benign tumor, an early cancer stage or advanced cancer stage, and any given type of cancer. In the latter example, the set of biomarkers may comprise thymidine kinase, C-reactive protein and/or any other biomarker selected at step 110 to include in the development of the diagnosis method. The level of each biomarker may be expressed in any unit that characterizes the presence of the biomarker in the body. Thus, an enzyme may be characterized by the level of its enzymatic activity, a protein, a hormone or any other biomarker may be expressed by a concentration level such as its mass or moles per volume of tissue or bodily fluid.

Step 140 represents the process of finding range values for each biomarker. For example, when considering thymidine kinase as a biomarker for cancer, a first range of zero units per liter (0 U/l) through five units per liter (5 U/l), a second range of five units per liter (5 U/l) through eight units per liter (8 U/l), and a third range of eight units per liter (8 U/l) and above may be defined as ranges for that specific biomarker.

Step 140 also involves discretizing the data, which comprises attributing a score number to each previously defined range of a biomarker level. Using the example of the three (3) thymidine kinase ranges above, the first range may be attributed the value zero (0), the second range may be attributed the value one (1) and the third range may be attributed the value two (2).

The discretization may be carried on other non-disease related data such as age. In the latter example, age may be selected for the diagnosis as a factor in the increase of the probability of having a target affection. Thus, age may be discretized such that a person of 0 to 20 years of age is attributed a value of "0", a person of 20 to 40 years of age may be attributed a value "1" and a person over 40 years of age may be attributed a value of "2". Sex may be discretized as "1" and "0" for female and male, respectively.

Step 150 represents computing an index value for each subject as follows:

$$I = \sum_{i=1}^{i=N} C_i \cdot L_i \qquad (1)$$

where the index value "I" for each subject may be the sum of the product of the score level "L" (e.g., computed at step 140) and a coefficient "C" associated with the "$i^{th}$" data input for a number "N" of data inputs (e.g., biomarker level, age, biometric data etc.). The coefficient "C" may be determined empirically as shown below at steps 160 and 170.

Step 160 represents applying one or more methods for segregating subjects using the health status data and the computed index values. For example, the method of segregation may be the Receiver Operating Characteristic (ROC) curve analysis. ROC curve analysis is a well known method in the medical field for determining whether a correlation between the level of a biomarker may serve as an indicator of the presence of a health condition. The latter is possible for example when there is a strong correlation between the amount of a substance in the body (e.g., high cholesterol) and a health condition (e.g., sclerosis of blood vessels).

Using the ROC curve analysis on the index values of all subjects in the group, it is possible to determine whether there is a cutoff value capable of classifying individuals into groups matching their health status. For example, if subjects carrying a disease are labeled as positive and the non-carriers are labeled as negative, the ROC curve analysis may yield a threshold that classifies the subjects into an above and a below-threshold groups matching the health statuses carrier and non-carrier of the disease, respectively. There may be false positives and false negatives for each chosen cutoff value in the range of possible values. The rate of success in determining true positive cases is called "Sensitivity", whereas the rate of success in determining true negative cases is called "Specificity". Sensitivity and specificity for a plurality of cutoff values are computed. Sensitivity and Specificity are rates, and thus may be expressed in the range of zero (0) to one (1), or as a percentage from zero (0) to one hundred percent (100%). The results are plotted as Sensitivity values versus one (1) (or 100% depending on the unit of choice) minus the corresponding specificity. The area under the curve (AUC) reveals whether ROC analysis may be a valid classifier of the data: the closer the AUC is to 100%, the better classifier is the ROC analysis. On the contrary, the ROC analysis may not be considered for classification purposes if the AUC is closer to 50%, which is considered close to a random process. In general, the ROC method of analysis may be considered valid, if the AUC is at least 0.8.

Moreover, each threshold value yields a "Sensitivity" and "Specificity". In populations where ROC analysis appears adequate, the "Sensitivity" curve decreases as the "Specificity" increases. At a particular threshold, the apex, the total of Sensitivity and Specificity is at a maximum. The apex is typically chosen as the threshold of classification if it yields a Sensitivity and Specificity each above 0.85, otherwise a threshold for Specificity and a threshold for Sensitivity may be respectively selected to yield a success rate of at least 0.85.

ROC analysis is one of any existing methods that may be utilized in embodiments of the invention to detect clusters in the data that define the clustering boundaries capable of segregating subjects into groups matching health status categories. For example, k-means clustering, hierarchical clustering, neural networks or any other clustering clustering method may be utilized in one or more embodiments of the invention. Furthermore, an embodiment of the invention may conduct the steps of FIG. 1 using a plurality of methods of clustering the data to achieve the results of the invention. The final clustering method that may be retained in any particular embodiment of the invention may be the one that yields the highest success rate of the diagnosis.

Step 170 represents computing success scores of the method of segregating of subjects in the test group. If the success level of the segregation into health categories is not satisfactory (e.g., no statistical difference compared to a population drawn from a random process), the parameters for computing the index values are revised and the analysis is repeated at step 140. The process of searching for optimal parameters may be repeated until the result of classification of subjects reaches (or exceeds) an acceptable success rate. Otherwise, if no optimal parameters may be found, the result may indicate that the chosen set of biomarkers is unsuitable for segregating the subjects based on the index method into the proposed health status categories.

The search for optimal parameters may involve changing one or more boundary values for discretizing biomarker values, and/or the weight coefficients associated with each biomarker in computing the index value for each subject. The search method may be manual i.e. an expert practitioner may set the initial parameters and adjust them, through multiple iterations of computation, while considering the outcome of the success rate of classification of subjects into health status categories. Implementations of the invention may also use numerical methods for automatic search to optimize parameters. Such methods comprise brute force search, where a large number of values of parameters and combinations thereof are tested. The numerical methods for determining optimal values may use gradient descent search, random walk search or any other mathematical method for searching for optimal parameters in order to achieve the goal of maximizing the success rate of the classification of subjects into correct corresponding health status categories.

Computer programs for conducting a search, in accordance with an implementation of the invention, require ordinary skills in the art of computer programming. Moreover, existing computer programs may be adapted (through a programming scripting language) to carry out a search process in an implementation of the invention. Computer programs include such programs as Mathematica™, Matlab™, Medcalc™, or any other available computer program may be used.

Step 180 represent the final step of determining the final parameters (or range thereof) that may be used in a diagnosis of the target disease(s). The optimal parameters include the coefficient associated with each biomarker, the number of ranges and the boundary values that define the ranges for each biomarker. Step 180 also includes determining the index range boundaries that define the categories as defined by the health status of subjects. The latter parameters may be used in systems for diagnosing whether a subject is a carrier of the a disease, as will detailed below in the method of use.

The invention provides a means for facilitating the display and read out of the results by defining the boundaries between ranges as discrete values for ease of use. For example, a scale comprising two health statuses, such as "disease present" and "disease not present", may be defined has having a discrete boundary, such as one "1", where the scale range lower than "1" may be mapped to "disease not present" status, while the scale range greater than "1" is mapped to "disease present" status.

Defining range boundaries as discrete values may be carried out during the search for the optimal parameters (as described above). The discrete range boundary values may also be provided computationally (e.g., using multipliers and offsets) subsequent to determining the optimal parameters.

FIG. 2A is a flowchart representing method steps involved in using a set of biomarkers in a diagnosis of one or more health statuses, in accordance with an implementation of the invention. Provided a set of pre-established optimal parameters that yield an acceptable success rate for classifying subjects into health categories based on a computed index from biomarkers, the invention provides a method and system for testing whether a new patient is likely a carrier of a suspected disease using biomarkers. Step 210 represents obtaining data from a patient. Similarly to step 130 and depending on the specific set of biomarkers involved in a diagnosis, bodily fluids, tissue and any other data necessary for the diagnosis are collected and the level of each biomarker is assessed.

Step 220 represents computing an index value for the patient. Provided the discretization boundary values for each biomarker, the level of each biomarker is converted into a score value, and provided the coefficient associated with each biomarker, the index value for the patient may be computed using equation (1).

Step 230 represents determining a patient's health status group. The patient's computed index value is compared to that of the established boundary values for health status categories. As described above, the established mapping between index values allows for ascertaining the health condition of a patient using its own index value.

Figure 2B:
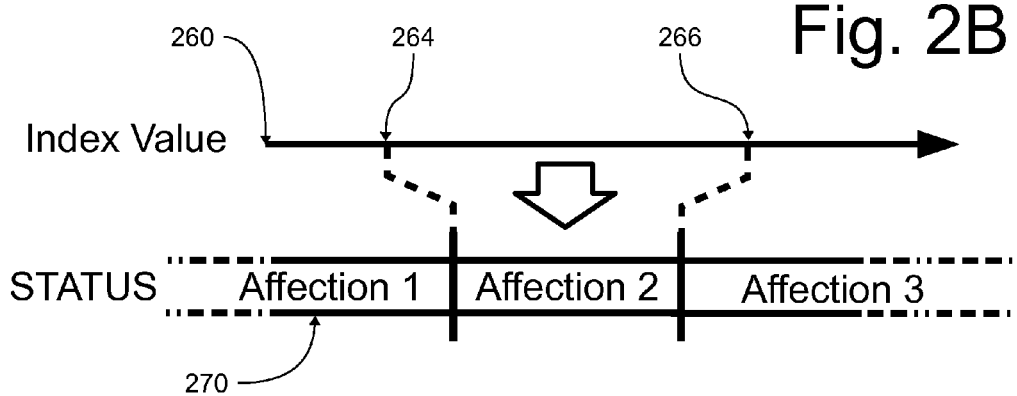
FIG. 2B is a graphical representation of a continuous index scale and defined index ranges corresponding health statuses as taught by the invention.

FIG. 2B is a graphical representation of a continuous index scale and defined index ranges corresponding to health statuses as taught by the invention. Line 260 represents a continuous scale of index values. Health status scale 270 represents the health status categories for which the diagnosis method was initially developed in accordance with the teachings of the invention. The health status scale may define two (2) or more health statuses, such as, in the case of cancer, non-carrier, benign tumor carrier and cancerous tumor carrier. Index values 264 and 266 may define the boundaries to read out the health status of a patient in question. Thus, a patient's index value that is less than about boundary 264 would indicate the patient in question is in a first health status category, an index value greater than about boundary 264 and less than about boundary 266 would indicate the patient is in a second health category while an index value greater than boundary 266 would indicate that the patient is in a third health status category. For example, a patient's index value may be within the range that matches the group of non-carriers of cancer, or the group of carriers of a benign tumor or the group of carriers of cancer.

The method steps as described in FIGS. 1, 2A and 2B may be carried out manually, i.e. a user may collect the data, compute the index value, then compare the index value to a pre-defined set of ranges to obtain the health status category of a patient and/or the method steps may be implemented in a machine (e.g., digital computer) that carries out any or all of the steps of obtaining the data, computing the index value, obtaining the health status category and displaying/communicating the health status category to a user.

An embodiment of the invention may be implemented in a way where the biomarkers data considered for developing a target diagnosis are collected in (healthy) subjects showing no symptoms of the target affection. By monitoring the subjects over time and determining which subjects develop an ailment, the invention allows for building a diagnosis (or a predictor index) for revealing the propensity of a subject to develop a target affection in a future time based on current biomarker data.

The benefits of developing an index-based scoring system, in accordance with one or more implementations of the invention, are numerous. The teachings of the invention allow a practitioner to compare results obtained from different individuals using a plurality of data combined in an index. For assessing progress in an individual (e.g., monitoring health condition during or post-treatment), a practitioner may conduct the tests using several biomarkers and follow the variations of the index values. For assessing the risk factors for an individual to develop a given disease, a practitioner may determine a range of index values and/or a variation thereof over time that may be indicative of the development of the disease. For example, some dog breeds are more susceptible than others to developing certain types of cancer. The index values provided by a diagnosis, in accordance with an implementation of the invention, may be utilized to spot those individuals that may be in the process of developing a cancer at an early stage.

Moreover, since a plurality of implementations of the invention may be developed for the diagnosis/detection of various aliments, a patient may be subjected only once to a test of a superset of biomarkers that would include biomarkers from several target diagnoses. By measuring the level of various biomarkers, more than one index may be computed at any time. The result is that each patient may be represented in a multidimensional space of indices that characterizes the state of the patient. Thus, a practitioner is provided a means to assess the probability for the patient to have one ailment versus another ailment when both present common symptoms.

System for Developing and Using a Multi-Biomarker Index

Figure 3:
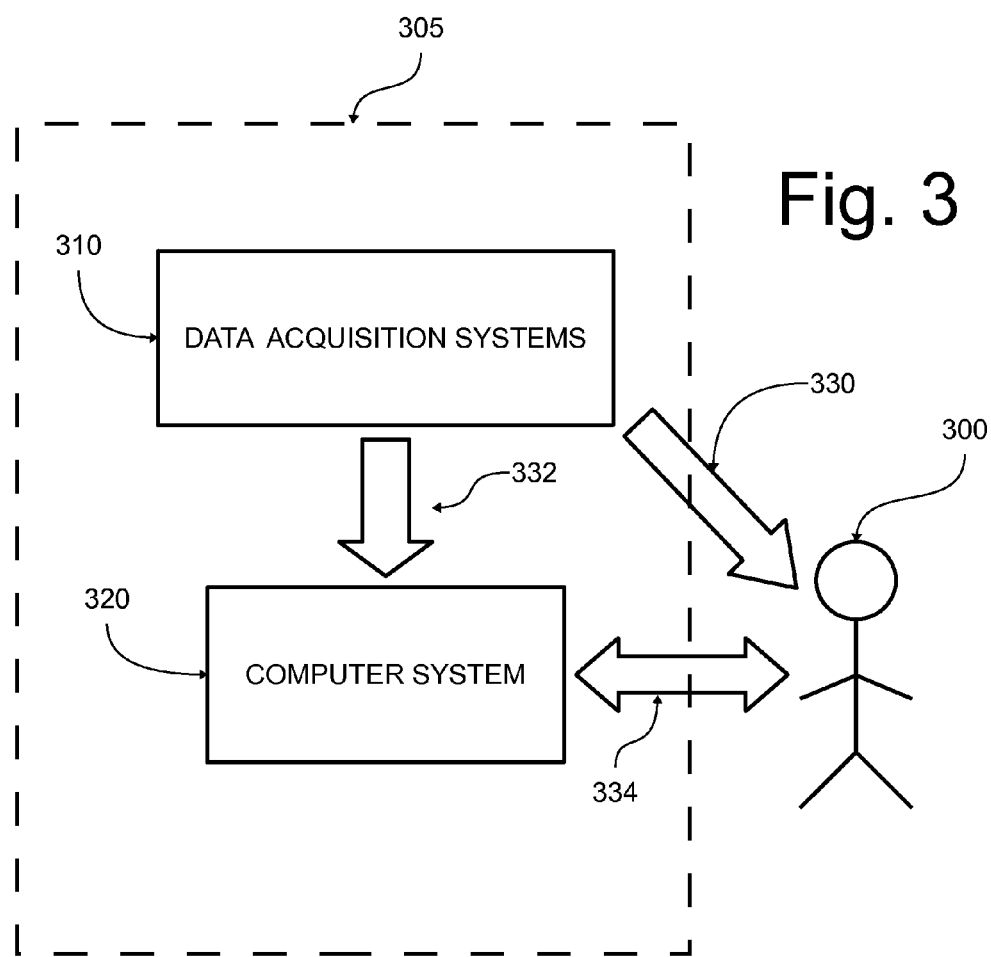
FIG. 3 is a block diagram representing components involved in the implementation of an embodiment of the invention.

FIG. 3 is a block diagram representing system components for implementing the development of use of diagnoses in accordance with an embodiment of the invention. The invention teaches the method steps described in FIGS. 1 and 2 as a general implementation of the development and use of diagnostic indices for any one or more target health affections in humans and/or animals. Furthermore, the invention teaches two-biomarker and three-biomarker methods for segregating canine subjects into groups affected by cancer, sepsis, SIRS. A system implementing an embodiment of the invention comprises one or more components for collecting data, one or more components for analyzing data, one or more components for communicating data with users.

Block 310 represents the data acquisition layer of any system that implements an embodiment of the invention. The system may be any system required for the acquisition of the biological data that may be associated with any particular target health affection for diagnosis or the development of a diagnosis thereof. For example, the biological data may require the measurement of the level of a particular substance in the blood (or in any other bodily fluid) and/or in an organ tissue. The substance may be a protein, a peptide, any type of hormone or any other molecule or ion the measurement of which may be relevant to the diagnosis of a particular health affection or the development of diagnosis thereof. In the case where a biomarker is a biological substance, Block 310 represents the necessary laboratory equipment for collecting biological samples and processing the samples in order to obtain the biological data required for a particular embodiment of the invention. For example, measuring a protein level in the blood requires many steps comprising collecting blood from subjects, separating the portion of blood that contains the protein (e.g., using a centrifuge), purifying the protein, submitting the a purified solution of the protein to a calibrated assay (e.g., using marked antibodies), or any other step that may yield the concentration of the protein in the blood sample. In other instances, the protein may be an enzyme, in which case it may be desirable to measure the concentration of the protein through its enzymatic activity level.

One with ordinary skills in the art of medical or veterinary diagnosis is able to recognize the laboratory method steps, and laboratory equipment represented by block 310 for collecting biological sample, extracting the pertinent biomarker, and measuring its level.

As described above in the definition of term "biomarker", the biological data may be any type of data that be involved in diagnosing a specific health affection whether the biological data may be assessed using a biological sample from the subject's body or through observational assessment of symptoms. For example, biological data comprise body temperature (e.g., in fever cases) heart beat rate, the number of siblings or parents having an affection (e.g., in cases of inherited affections), the elapsed time since the first signs of a disease started to show symptoms or any other non-substance related measurement that may be obtained from a patient and that may be considered in a diagnosis. Block 310 represents the tools and equipments necessary for collecting the biological data, which is accessible to one with ordinary skills in the pertinent art.

Block 320 represents a computer system for implementing and executing computer program instructions following the teachings of the methods developed in an embodiment of the invention. The computer system is any analog and/or digital computer capable of being configured to take input data, execute some or all of the method steps of the invention and provide the result of such execution to a user.

The computer system 320 may be a digital computer having a digital processor, a memory, a data transfer bus, a storage medium and any electronic communication means that allows the computer to receive and send data through display and communication to and from users and/or other machines. In embodiments of the invention, the computer may be embedded (as symbolized by block 305) in a device for carrying out medical (or veterinary) tests. Thus, a mobile and/or portable system comprises a device configured to collect the data such as determining the level or one or more biomarker level in a blood sample, and a computer system for carrying the steps of the invention. The device may be enabled with display means such that the results are communicated to a user.

In other embodiments of the invention, the computer 320 may stand alone, such as a computer system that is detached from any particular a device, while being capable of receiving data through direct communication (e.g., user interface), and/or remote communication means (e.g., networked data transfer).

The input data may be any of the biological and non-biological data, described above, that may be entered to the computer automatically through one or more links 332, or through a user interface 334 provided to a user 300. For example, a practitioner 300 may obtain the biological data from the data collection system through one or more communication (or interface links) 330, then enter the data into the computer system through the computer interface 334.

The practitioner may also enter in the computer system further configuration data, such as range boundaries for data discretization, optimization method or any other configuration data to conduct a search for optimal parameters. The computer system comprises program instructions to conduct a search for optimal parameters. Computer system 320 contains program instructions the execution of which allows to discretize new data (e.g., from a patient) compute one or more indices, then compare the new data to previously generated (or stored data) in order to provide a diagnosis.

In embodiments of the invention, a computer program as well as the data for any particular diagnosis method, in computer system 320, may be replicated from one machine to another, thus, allowing the diagnosis programs to be replicated to any number of other machines. For example, in portable blood test devices, a computer program may be configured to process the data and provide fast diagnosis using pre-stored diagnosis parameters.

However, the data acquisition system may be separated and remotely located and may serve the practitioner remotely. For example, the computer program may be implemented on a central unit that may be used to collect biological data from a plurality of data acquisition systems (e.g., using computer networks), and serve client machines with diagnoses as they may be entered remotely. Furthermore, the collection of data from a plurality of client data acquisition system may serve to further refine the diagnosis program as more and more data become available.

The computer system 320 through the interface 334 may process the output results for display and communication to the user. For example, the result of one or more tests may be graphically generated and printed out onto a video screen or a paper printer.

The data may be presented as raw numbers, in a form of graphical display, such as charts and curves, icons for indicating the presence or absence of an affection and the severity thereof, or any other available means for communicating computer data to a user.

Method of Detecting Cancer and Sepsis

An embodiment of the invention targets the diagnosis of cancer and sepsis in a typical patient i.e. showing general symptoms of inflammation while failing to reveal the underlying affection. Inflammation may be caused by a number of factors including cancer, infection, trauma and many other factors. A method according to the invention may use the measurement of the biomarkers thymidine kinase (TK) and c-reactive protein (CRP) to distinguish between whether a patient is affected by one and/or the other disease. In another embodiment of the invention, the set of biomarkers additionally includes the hormone C-type Natriuretic Peptide (CNP). According to the method steps described in FIG. 1, the development of a diagnosis starts with the specification of one or more target affections, and a set of data (e.g., biomarkers) that will be used in the diagnosis method. Below is a brief introductory description of TK, CRP and CNP's involvement in cancer, inflammation and sepsis. The details of the mechanisms involved in the variations of the latter biomarkers in the affections in question are beyond the scope of the present disclosure, but are readily available in the literature.

There has been a long standing and studied relationship between cancer and inflammation. The inflammatory response orchestrates host defenses to infection, trauma, toxins, or other tissue damaging events and mediates tissue repair and regeneration. Epidemiological evidence points to a connection between inflammation and a predisposition for the development of cancer, i.e. long-term inflammation leads to the development of dysplasia. Thus, while acute inflammation is normally tightly controlled and part of the healing process, chronic inflammation may be associated with a number of diseases including cancer.

In cancer, there is evidence that inflammation plays an essential role at each stage of the disease (initiation and proliferation), and both tumor and inflammatory cells are able to directly or indirectly either inhibit or stimulate tumor growth. The effectiveness of tumor development has been demonstrated to correlate directly with the degree of the inflammatory reactions, and it seems that there are interactions between the cytokines produced in response to inflammatory reactions and tumor growth and even indications that inflammatory cytokines favor tumor promotion. Furthermore, with the assistance of inflammation, tumor cells infiltrate neighboring tissues, enter into the bloodstream, migrate, and establish remote colonies i.e. metastases.

With the inflammatory process initiating the acute-phase reaction the generation of acute-phase proteins (APP) occurs. C-reactive protein (CRP) is a major APP and has been shown to be an effective measure of general inflammation. The concentration of CRP or any serum APP level correlates to both the severity and duration of the inflammatory stimuli.

The term "sepsis" is often used to describe a variety of conditions relating to systemic manifestations of inflammation accompanied by an infection. In the truest sense sepsis is reserved for those conditions whereby the host is overwhelmed by an infection causing the immune system to overreact resulting in organ failure and death. However, sepsis is also used more loosely to describe a major infection such as "septicemia". The similarities that exist between an acute inflammatory response secondary to both infectious and non-infectious causes and the severe diagnostic and therapeutic management challenges that ensue, definitions have been provided for "Systemic Inflammatory Response Syndrome" (SIRS), which describes a severe systemic insult to an infectious or non-infectious insult.

Sepsis is actually a continuum of a disease process that begins with Systemic Inflammatory Response Syndrome (SIRS) consisting of sepsis, severe sepsis, and septic shock. SIRS is the systemic inflammatory response that may occur due to a variety of severe clinical insults—both infectious and non-infectious. The response is manifested by the following conditions:

SIRS in Humans—presence of 2 or more criteria from the following:
Temperature <97° F. or >100° F.
Heart rate >90 beats/min
Respiratory rate >20 breaths/min or PaCO2 <32 mmHg
WBC >12,000 cells/mm$^3$, <4,000 cells/mm$^3$
SIRS in Dogs—presence of 2 or more criteria
Temperature <100.4° F. or >104° F.
Heart rate >120 beats/min
Respiratory rate >20 breaths/min or PaCO2 <30 mmHg
WBC >16,000 cells/mm$^3$, <6,000 cells/mm$^3$
SIRS in Cats—presence of 3 or more criteria
Temperature <100° F. or >103.5° F.
Heart rate <140 beats/min or >225 beats/min
Respiratory rate >40 breaths/min
WBC >19,500 cells/mm$^3$ or, <5,000 cells/mm$^3$ (or 5% bands)

Sepsis is the systemic response to an infection. This systemic response is manifested by two or more of the above-mentioned SIRS criteria as a result of proven or suspected infection. Severe sepsis is classified as sepsis associated with organ dysfunction, hypoperfusion or hypotension. Hypoperfusion and perfusion abnormalities may include, but are not limited to, lactic acidosis, oliguria, or an acute alteration in mental status. Septic shock is classified as severe sepsis with hypotension, despite adequate fluid resuscitation, along with the presence of perfusion abnormalities that may include, but are not limited to, lactic acidosis, oliguria, or an acute alteration in mental status. Patients who are on inotropic or vasopressor agents may not be hypotensive at the time that perfusion abnormalities are measured.

An infection may or may not occur in the presence of SIRS. Sepsis is caused by a bacterial infection that can begin anywhere in the body. Common places where an infection might start include:

The bowel (usually seen with peritonitis)
The kidneys (upper urinary tract infection or pyelonephritis)
The lining of the brain (meningitis)
The liver or the gall bladder
The lungs (bacterial pneumonia)
The skin (cellulitis)

Sepsis or septic shock occur only when SIRS occurs with an infection. Sepsis develops when the immune system becomes over activated in response to an existing infection, setting in motion a cascade of dangerous inflammatory and coagulation responses throughout the body. This immunological response causes widespread activation of acute-phase proteins, affecting the complement system and the coagulation pathways, which then cause damage to the vasculature as well as to the organs. Various neuroendocrine counter-regulatory systems are then activated often compounding the problem. Even with immediate and aggressive treatment, this may progress to multiple organ dysfunction syndrome and eventually death.

An embodiment of the invention combines a set of biomarkers comprising thymidine kinase. Thymidine kinase has been well studied in both human and veterinary applications. TK is commonly expressed by a wide array of neoplasms, both benign and malignant. Historically, research has been centered on hematopoietic cancers such as leukemia and lymphoma where serum levels of TK reach high concentrations. More recently, TK has been shown to be expressed by a wide array of sarcomas, such as hemangiosarcoma.

Thymidine kinase type 1 (TK) is a cytosolic enzyme involved in DNA synthesis through the so called "salvage pathway" for thymidine biosynthesis, in which deoxythymidine is converted to deoxythymidine monophosphate, leading to its eventual incorporation into DNA. Cellular TK activity is closely correlated with the DNA synthesis phase of the cell cycle. As such, its expression is restricted to proliferating cells, and thus is often more highly expressed in malignant cells, which are characterized by dysregulated proliferation.

The set of biomarkers, in the embodiment of the invention, comprises c-reactive protein (CRP). The acute-phase reaction (APR) is a nonspecific phenomenon of the innate immune response characterized by an increase in certain plasma proteins (acute-phase proteins) after tissue damage. The purpose of the acute-phase response is to prevent ongoing tissue damage, isolate and destroy the infective organism (if any) and activate the repair processes necessary to restore the host/organism's normal function. APR is characterized by leukocytosis, fever, alterations in the metabolism of many organs as well as changes in the plasma concentrations of various acute-phase proteins (APP). APP have been defined as any protein whose plasma concentrations increases (positive acute-phase proteins; fibrinogen, serum amyloid A, albumin, C-reactive protein) or decreases (negative acute-phase proteins; albumin, transferrin, insulin growth factor I) by at least 25 percent during an inflammatory disorder. In most mammals, C-reactive protein (CRP) is a major APP and has been shown to be an effective measure of general inflammation. The concentration of CRP or any serum APP level correlates to both the severity and duration of the inflammatory stimuli.

In accordance with the teachings of the invention, it should be implicit that CRP is used as a biomarker that represents the family of biomarkers involved in acute-phase reaction.

In another embodiment of the invention, the set of biomarkers comprises the hormone C-type natriuretic peptide (CNP). CNP is a member of the vaso-dilating family of the natriuretic peptides, and has the weakest vaso-dilating effect as compared to A-type (ANP) and B-type (BNP). Whereas ANP and BNP are produced primarily in the heart, CNP is primarily produced by the vascular endothelium cells and macrophages in response to several stimuli including inflammatory mediators such as tumor necrosis factor, interleukin-1β and transforming growth factor-β that are known to be important in the pathogenesis of sepsis. Perhaps more importantly, microbial products like lipopolysccharide directly stimulate CNP production. C-type natriuretic peptide is a particularly interesting biomarker for sepsis because CNP may be important in the innate immune response to infection. CNP exhibits antimicrobial activity by both inhibiting microbial growth and by modifying the pathogenecity of microorganisms. Patients with septic shock have significantly greater serum of CNP concentration than do healthy subjects and those with congestive heart failure, hypertension and chronic kidney disease.

Thus, systemic inflammation is driven by tissue damage and the subsequent activation of the repair process through the acute phase reaction. The invention considers three primary drivers to the inflammatory process, neoplasia, infection (sepsis), and trauma. The invention teaches that by the integration of three biomarkers into a "neoplasia index" and a "sepsis index", the three unrelated processes together, namely cell division of abnormal cells as gauged by the level of TK, the response by the vasculature to an infectious insult as gauged by the level of CNP, and a measure of general inflammation as gauged by the level of CRP, an embodiment of the invention may detect whether the cause of the general inflammation is caused by cancer or sepsis.

TK, CRP and/or CNP levels may be assessed through any available method for measuring their levels, whether directly or indirectly. For example, in embodiments of the invention, the level of CNP may be indirectly assessed by measuring a byproduct (pCNP) of the proteolytic cleavage of the precursor (proCNP) that produces CNP. The intracellular proteolysis of proCNP produces, in equimolar amounts, CNP and the N-terminal fragment (pCNP) which may be measured. Therefore, the concentration of pCNP is a good indicator of the level of release of CNP. The actual concentration of CNP (as compared with that of pCNP) may differ depending on the speed at which both molecules are eliminated. In the disclosure, a reference to CNP concentration may be interpreted as a reference to the concentration of CNP proper, or any of the related biomarkers (e.g., proCNP and/or pCNP) that indirectly assess the level of CNP.

Cancer Detection and Screening in Dogs Using TK and CRP

In accordance with the method of the invention described in FIG. 1, an embodiment of the invention targets the detection of cancer or the propensity to develop cancer using two or more biomarkers. To the latter end, a study involving 356 dogs was conducted to evaluate a dual biomarker method. At the start, the recruited dogs were "apparently healthy" i.e. with no overt signs of illness or history of cancer. The subjects were monitored for their health status. Over a period of time, the health status (e.g., presence versus non-presence of cancer) is matched with the levels of the biomarkers as measured initially in each subject.

The goal is two-fold: 1) to establish a method of detection of cancer in a subject suspected of having cancer (i.e. diagnosis method), and 2) to establish a method for detecting a propensity to develop cancer before subjects develop signs of cancer (i.e., screening method). In both methods the subjects are classified on the basis of their health status as being affected by cancer (as diagnosed through other methods e.g. histology) or unaffected. To establish a method of detection, the study uses the levels of biomarkers as measured at the time of detection of cancer. On the other hand, the study uses the level of biomarkers as initially measured at the start of the study.

Thus, subsequently by measuring the level of the biomarkers in a subject, the method allows a practitioner to use the results as a diagnosis of current health status and/or as a predictor of the risk that a subject would eventually develop cancer.

Out of the 356 dogs recruited for the study, 378 dogs were enrolled and 22 disqualified due to prior history of cancer or inadequate specimen to complete analysis. The details of the cohorts breed and recruitment is shown in Table 1, and the cohort's sex distribution is shown in Table 2. In the latter study the biomarkers chosen were thymidine kinase (TK) and a canine-specific c-reactive protein (c-CRP). After the initial measurement of the biomarkers, the subjects were monitored and tested for cancer over a period of several months.

TABLE 1

Breed details of the cohort

| Breed | Total | Total Disqualified | Total Included |
|---|---|---|---|
| German Shepherd | 173 | 11 | 162 |
| White Shepherd | 8 | 0 | 8 |
| Golden Retriever | 193 | 11 | 182 |
| Portuguese Water dog | 4 | 0 | 4 |
| Total Dogs | 378 | 22 | 356 |

TABLE 2

Sex distribution of the cohort

| Sex | Total | Total Disqualified | Total Included |
|---|---|---|---|
| Female | 84 | 4 | 80 |
| Female Spaded | 111 | 6 | 105 |
| Male | 97 | 6 | 91 |
| Male Neutered | 74 | 5 | 69 |
| N/A | 12 | 1 | 11 |
| Total | 378 | 22 | 356 |

Table 3 shows the types of cancer as confirmed through histological or cytological tests, or by observation when the subjects

TABLE 3

Cancer types detected in the cohort

| | Cancer Types | Total |
|---|---|---|
| Histological/ Cytological Conformed Cancers | Leukemia Hemangiosarcoma Sarcoma Lymphoma Hemangiosarcoma Single Cell Carcinoma | 6 |
| Observational Based | Hemangiosarcoma Lymphoma Hemangiosarcoma Parathyroid | 4 |
| | Total Cancers | 10 |

Figure 4A:
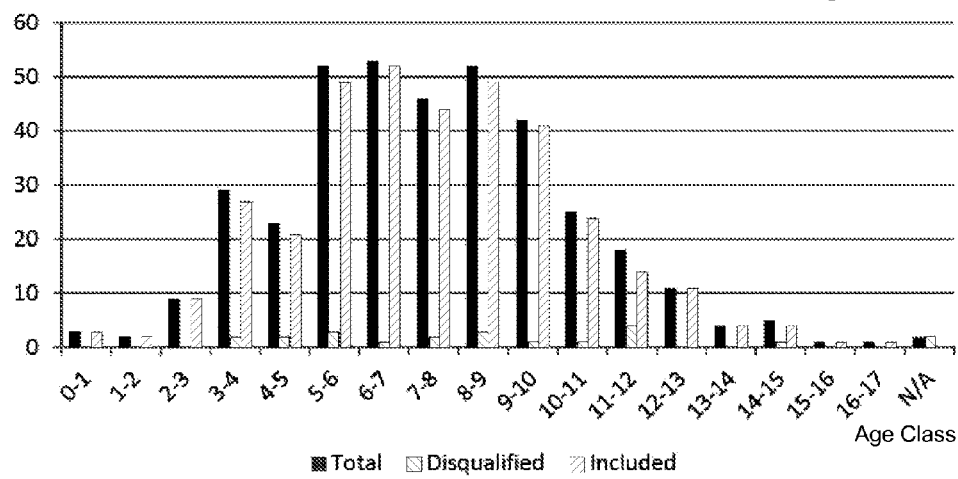
FIG. 4A shows a histogram of the age distribution of the cohort of dogs involved in one study.

FIG. 4A shows a histogram of the age distribution of the cohort of dogs involved in the study. FIG. 4A shows the distribution of the total number of subjects in each class (i.e., age group) involved in the study, the number of disqualified subjects and the number that were included in the development of the cancer detection method.

The measurement of Thymidine kinase enzymatic activity in samples of blood plasma is described in U.S. Pat. No. 8,097,432 B2, which is included herewith in its entirety by reference. In brief, a blood plasma is separated from a sample of blood to be tested for TK activity. The plasma is introduced into a solution containing an analog of deoxythymidine nucleotide and a phosphate donor. The product of the enzymatic activity is then measured using an immunoassay.

The measurement of CRP may be carried out using any available method for extracting and measuring protein concentration in a bodily fluid or tissue. The latter methods comprise using centrifugal force, electrophoresis, chromatography, immuno-binding assays and any available method for measuring the concentration of a protein.

Figure 4B:
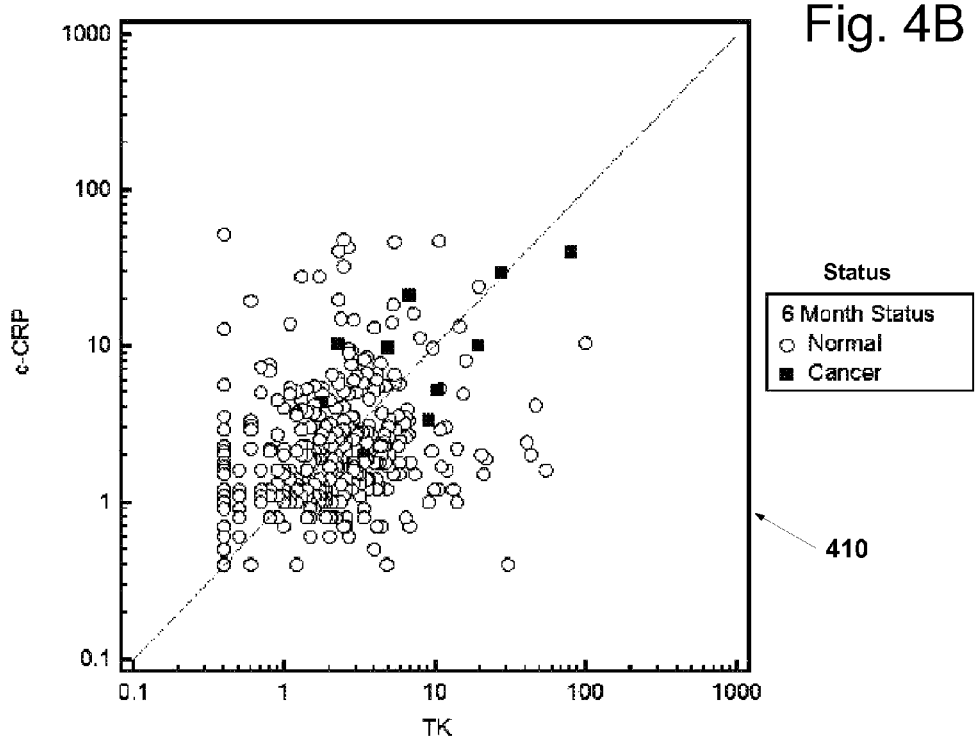
FIG. 4B shows a scatter plot representing cohort data for TK and CRP at six months status from the start of a study to develop a diagnosis method according to the invention.

FIG. 4B shows a scatter plot representing cohort data for TK and CRP at six month status from the start of the study. Plot 410 shows data points defined by the level of TK (abscissa), level of CRP (ordinate) and whether the subject was had cancer (square) or did not (circle). The scatter plot visually reveals that the dogs affected by cancer (as represented by squares) have a relatively high levels of both c-CRP and TK, and that these two biomarkers are correlated (follow the diagonal line) pointing to the association of inflammation with cancer.

Using TK and CRP in the latter study, and in accordance with the invention as described by formula (1) and FIG. 1, a two-parameter neoplasia index may be computed, by applying equation (1), as follows:

$$N_2 = a_2 \cdot dTK + b_2 \cdot dCRP \quad (2)$$

Where "$N_2$" denotes the Neoplasia index in a two (2) parameter model using TK and CRP, and where "$a_2$" and "$b_2$" denote the coefficients associated with TK and CRP, respectively. "dTK" and "dCRP" denote the discrete score value matched with a range of TK level and CRP level, respectively. As described above, TK level may be represented by the level of its enzymatic activity, whereas CRP may be represented by its mass (or moles) per volume of blood plasma.

As described above, the level of the biomarkers was measured and discretized. A discrete score is assigned to ranges of the levels for each biomarker. Table 4.0 and Table 4.1 show the details of the discretization scores corresponding to ranges for each of TK and CRP level as used in diagnosing and screening for cancer, respectively.

TABLE 4.0

Discrete scores for TK and CRP ranges used for cancer diagnosis

| TK (U/L) | c-CRP (mg/L) | Score |
|---|---|---|
| 0 to 1.7 | 0 to 3.9 | 0 |
| 1.8 to 4.0 | 4.0 to 9.5 | 1 |
| 4.1 to 7.0 | 9.5 or greater | 2 |
| 7.1 or greater | | 3 |

TABLE 4.1

Discrete scores for TK and CRP ranges used for screening

| TK (U/L) | c-CRP (mg/L) | Score | |
|---|---|---|---|
| 0 to 1.7 | 0 to 1.9 | 0 | |
| 1.8 to 5.9 | 2 to 3.9 | 1 | 0 if TK ≤ 1.7 U/l |
| 6.0 or greater | 4.0 to 9.5 | 2 | |
| | 9.6 or greater | 3 | |

TABLE 4.2

Coefficients for Equation (2)

| Method | $a_2$ | $b_2$ |
|---|---|---|
| Diagnosis | 1.7 | 2.32 |
| Screening | 2.1 | 1.6 |

In the discretization scheme in Table 4.1, and in other cancer tests (e.g., see below), when a patient's level of TK is close to zero, the discrete value assigned to CRP may also be assigned the value zero regardless of the measured value for CRP.

Using the discretization schemes provided in Table 4.0 and Table 4.1 and the coefficients provided in Table 4.3 in formula (2), an index value lower than "0" would indicate low probability a patient has cancer versus a value of one (1) or greater, which would indicate that the patient has cancer.

In the latter study, the subjects were followed over time, and tests were carried out at four (4) months, and six (6) months from the initial test. Other (histological) tests were also carried out to confirm the presence of cancer.

For comparison of the performance of the method provided by the invention versus previous methods that relied solely on a single biomarker (e.g., TK), Receiver Operating Characteristic (ROC) analysis has been carried out using TK alone or the two-biomarker implementation of the invention. The ROC curves representing Sensitivity vs. one hundred (100) minus Specificity is plotted in FIGS. 5, 6 and 7, and the area under the curve is computed and shown in Table 5.

TABLE 5

ROC AUC for TK vs. Neoplasia Index

| Status | TK Only | Neoplasia Index (TK&CRP) |
|---|---|---|
| Confirmed Cancer | 0.783 | 0.941 |
| 4-Months Status | 0.889 | 0.970 |
| 6-Months Status | 0.826 | 0.930 |

FIG. 5 shows plots of the Receiver Operating Characteristic (ROC) curves Sensitivity vs. one hundred (100) minus Specificity using TK alone and the two-biomarker implementation of the invention following confirmation of cancer in a subset of subjects. Plot 510 shows the plot of the ROC curve for TK. The area under the curve (AUC) is 0.783 (or 78.3%). At value level of TK of 2.25 U/l or greater, the Sensitivity is 0.85 (or 85%), and the Specificity is 0.537 (or 53.7%). Plot 550 shows the ROC curve for the index computed using formula 2 with discrete values using table 4.0. The UAC in plot 550 is 0.941 (or 94.1%). Using the threshold value for the index of 4.2, the Sensitivity is 100% and the Specificity is 80%. Therefore, the predictive power of the method is greater when using the two-biomarker neoplasia index than by using TK alone to diagnose cancer dogs.

FIG. 6 shows plots of the ROC curves Sensitivity vs. one hundred (100) minus Specificity using TK alone and the two-biomarker implementation of the invention at four (4) months from the initial test. Plot 610 shows the ROC curve plot using TK data alone. The AUC in plot 610 is 0.889 (88.9%). Above a threshold of 4.8 U/l, the ROC analysis yields a Sensitivity of 91.7%, and the Specificity of 83.6% success rate. Plot 650 shows the ROC curve for the neoplasia index computed using data collected at 4 months. The AUC in plot 650 is 0.97 (or 97%), and above an index value of 5.3, the Sensitivity is 100% and the Specificity is 89.9%. As expected, the success rate of the ROC analysis has increased at 4 months due to the increase of TK along with the progression the cancers. However, using the neoplasia index provided by the invention, the AUC, the Sensitivity and the Specificity are greater than using TK alone.

FIG. 7 shows plots of the ROC curves Sensitivity vs. one hundred (100) minus Specificity using TK alone and the two-biomarker implementation of the invention at six (6) months from the start of the study. Plot 710 shows the ROC curve plot using TK data alone. The AUC in plot 710 is 0.826

(82.6%). Above a level of TK of 2.858 U/l, the Sensitivity is 85.7% and the Specificity is 66.0%. Plot 750 shows the ROC curve for the neoplasia index computed using data collected at 6 months. The AUC in plot 750 is 0.93 (or 93%), and above an index value of 4.2, the Sensitivity is 90% and the Specificity is 80.6%. As with previous assessments, using the two-biomarker neoplasia index yields a higher success rate for distinguishing patients carrying cancer from the non-carriers.

Cancer Workup

One of the most difficult of health status determinations is benign vs. malignant neoplasia. In a previous study of hemoabdomen dogs, TK was evaluated for its effectiveness in separating the emergency workup of hemoabdomen dogs for benign vs. malignant disease. In a mufti-institutional study of 38 dogs, 26 had malignant cancer and 12 were benign. Table 6 shows the details of benign and malignant cancer types in the latter study.

TABLE 6

Benign vs. Malignant Cancer types detected in the cohort

| Benign | Malignant |
| --- | --- |
| Hematoma | Sarcoma |
| Fibro nodule | Hemangiosarcoma |
| NLH | Lymphoma |
| Myelolipoma | Leukemia |
| Fibrous lipoma | Parathyroid Cancer |
| Hemangioma | |

Figure 8:
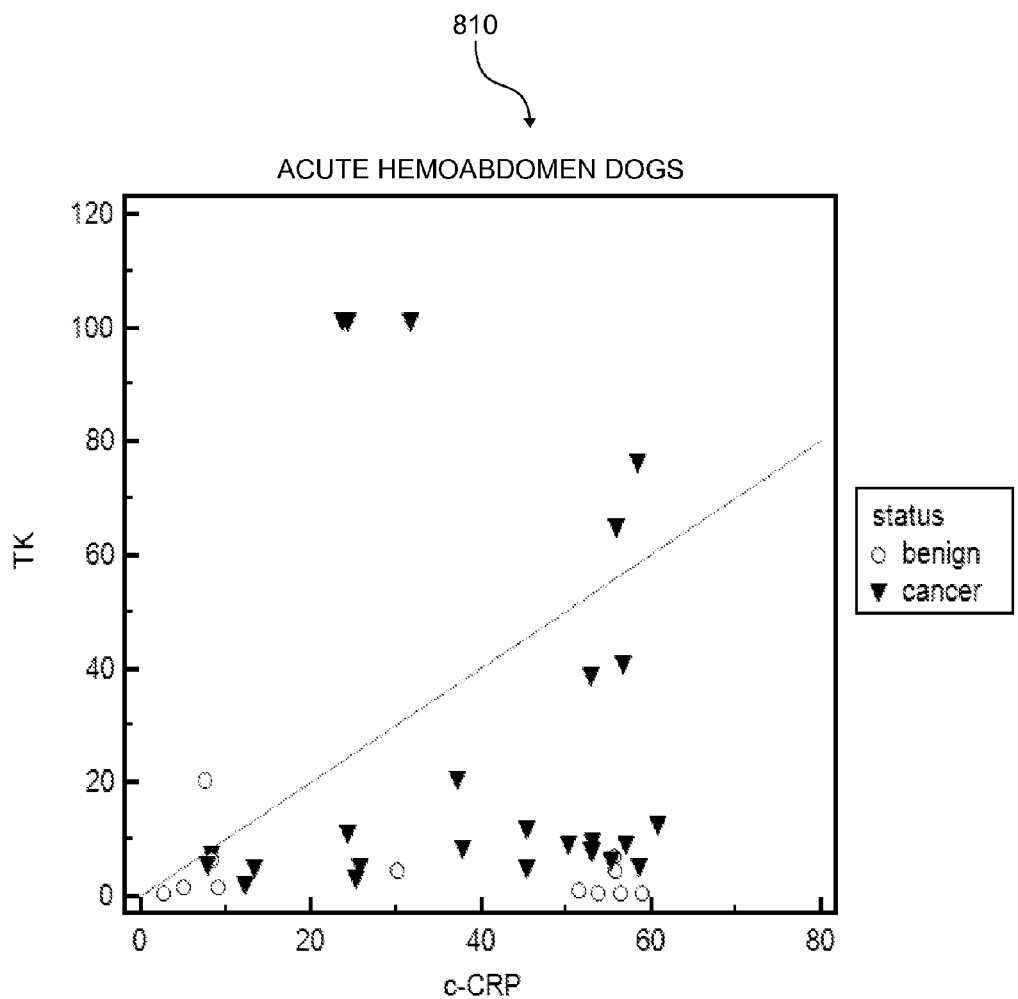
FIG. 8 shows a scatter plot representing TK vs. c-CRP data in a group of hemoabdomen dogs.

FIG. 8 shows a scatter plot representing data in the cancer workup group. Plot 710 represents data points defined by the level of CRP (abscissa), level of TK (ordinate) and whether a subject had a malignant (triangle) or benign (circle) tumor. The scatter plot visually reveals that the dogs affected by malignant cancer (as represented by squares) have a relatively high levels of both TK and CRP.

In the latter study, the data have been discretized according to the two-biomarker method described above, and the neoplasia index computed for each subject. The data were analyzed using the ROC analysis while considering TK levels alone and the neoplasia index.

FIG. 9 shows plots of the Receiver Operating Characteristic (ROC) curves Sensitivity vs. one hundred (100) minus Specificity using TK alone and the two-biomarker implementation of the invention while considering malignant cancer vs. benign cancer. Plot 910 shows the plot of the ROC curve for TK. The area under the curve (AUC) is 0.878 (or 87.8%). The analysis in plot 910 shows that above a value of 6.5 U/I of TK, the Sensitivity is 69.2% while the Specificity is 85%. Plot 950 shows the ROC curve for the index computed using formula 2 with discrete values using table 4.0. The AUC in plot 950 is 0.925 (or 92.5%), and a neoplasia index value above the criterion value of 8.16, the Sensitivity is 76% and the Specificity is 85%. Therefore, the predictive power of the method is greater by using the neoplasia index than by using TK alone in order to determine whether a cancer is benign or malignant.

Cancer Detection in Dogs Using TK, CRP and CNP

As described above, inflammation is highly reactive during an infection. In the acute care setting, understanding the primary source of inflammation and associated illness is urgently required. In this setting the inclusion of a sepsis parameter may help to separate cancer cases from sepsis and trauma cases.

To develop a diagnosis method that not only targets cancer, but also a separation of cancer from sepsis cases, an embodiment of the invention further considers using proCNP as a biomarker in addition to TK and CRP. In a study to determine the parameters necessary for the diagnosis method, a cohort of 36 SIRS dogs with fever from a university acute care facility were evaluated and diagnosed. TK, CRP, and CNP levels were measured in the serum of every subject in the group. The cohort consisted of seven (7) subjects having been diagnosed with cancer, fourteen (14) subject having been diagnosed with sepsis and fifteen (15) having been diagnosed with SIRS.

Using TK, CRP and CNP, a three-biomarker neoplasia index may be computed, by applying equation (1), as follows:

$$N_3 = a_3 \cdot dTK + b_3 \cdot dCRP - c_3 \cdot dCNP \qquad (3)$$

Where "$N_3$" denotes the Neoplasia index in a three-biomarker method using TK, CRP and CNP, and where "$a_3$", "$b_3$" and "$c_3$" denote the coefficients associated with TK, CRP and CNP, respectively, in the 3-biomarker method of neoplasia index. TK level may be represented by the level of its enzymatic activity, whereas CRP and CNP may be represented by their mass (or moles) per volume of blood plasma. "dTK", "dCRP" and "dCNP" denote the discrete score value matched with a range of TK level, CRP level and CNP level, respectively.

FIG. 10 shows scatter plots representing data in a group studied for cancer and sepsis. The data points of plot 1010 represent the level of CRP (abscissa), the level of TK (ordinate) and whether the subject had a cancer (triangle) or other ailment (circle). Plot 1010 visually reveals that the dogs affected by cancer (as represented by squares) have a relatively high levels of both TK and CRP, as described above. The data points of plot 1050 represent the level of CNP (abscissa), the level of TK (ordinate) and whether the subjects have a cancer (triangle) or other ailment (circle). Plot 1050 visually reveals that the dogs affected by cancer (as represented by triangles) have a relatively high levels of both TK and CNP pointing out the association discussed above between cancer and sepsis.

Inflammation may be due to sepsis, neoplasia, or both. To separate cancer cases from SIRS/sepsis cases the inclusion of CNP contributes additional information. Thus, allowing in the ROC analysis the cutoff for TK to be reduced substantially to improve sensitivity and specificity.

In accordance with the teachings of the invention, as described in FIGS. 1 and 2, the parameters for computing the three-biomarker neoplasia index were optimized to maximize the separation power of the index of the sub-groups of subjects based on their respective health status.

Table 7 shows the detail of the discretization scores corresponding to ranges for each of TK, CRP and CNP ranges in the three-biomarker method for diagnosing subjects with cancer vs. subjects with sepsis.

TABLE 7

Discrete scores for TK, CRP and pCNP ranges

| TK (U/L) | c-CRP (mg/L) | pCNP (pmole/L) | Score |
| --- | --- | --- | --- |
| 0 to 1.7 | 0 to 3.9 | 0 to 3.8 | 0 |
| 1.8 to 4.0 | 4.0 to 9.5 | 3.9 to 11.4 | 1 |
| 4.1 to 7.0 | over 9.5 | over 11.5 | 2 |
| over 7.1 | | | 3 |

In the latter three-biomarker method, the coefficients "$a_3$", "$b_3$" and "$c_3$" of formula (3) are given the values 1.63, 2.18 and 1.68, respectively, when using the method for screening.

Figure 11:
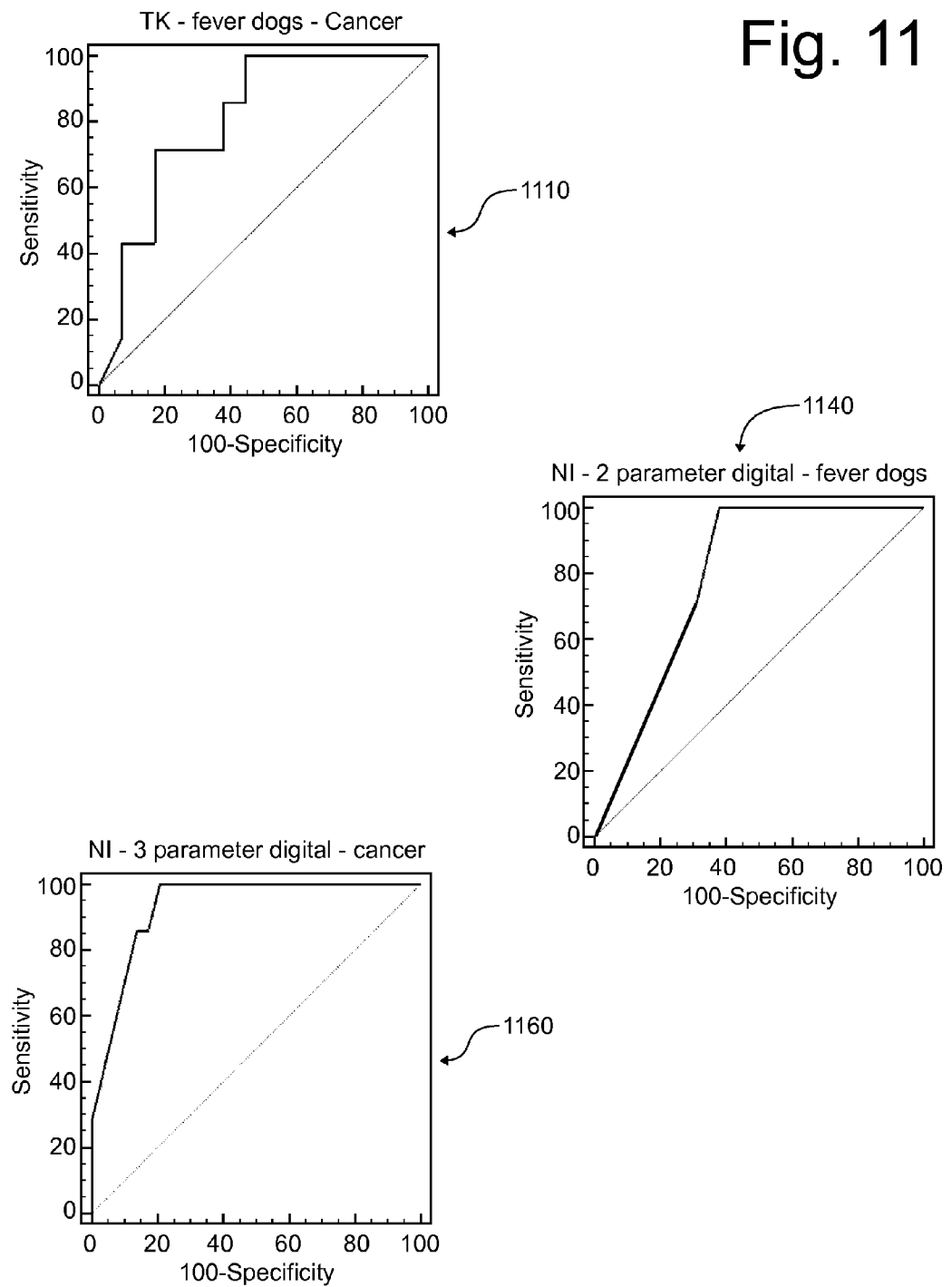
FIG. 11 shows plots of the Receiver Operating Characteristic (ROC) curves Sensitivity vs. one hundred (100) minus Specificity results of using TK data alone, using the two-biomarker (i.e., TK and CRP) method, and using the three-biomarker (TK, CRP and CNP) while considering subjects with cancer versus subjects diagnosed with other affections.

FIG. 11 shows plots of the Receiver Operating Characteristic (ROC) curves Sensitivity vs. one hundred (100) minus Specificity results of using TK data alone, using the two-biomarker (TK and CRP) method and using the three-biomarker (TK, CRP and CNP) in subjects with cancer and other subjects diagnosed with other affections. Plot 1110 shows the ROC curve for TK alone. The area under the curve is 0.808 (or 80.8%). The criterion value 18.7824 U/l of TK yields a Sensitivity of 42.9% and a Specificity of 85.0%.

Plot 1140 shows the ROC curve for the two-biomarker neoplasia index (i.e., based on TK and CRP). The AUC in the latter case is 0.791 (or 79.1%). The criterion value is greater than 8.16 yields a Sensitivity of 71.4% and a Specificity of 69.0%.

Plot 1160 shows the ROC curve for the three-biomarker method (i.e., based on TK, CRP and CNP). The AUC in the latter case is 0.933 (or 93.3%). The criterion value for the three-biomarker index of 5.99 yields a Sensitivity of 85.7% and Specificity of 85.0%. As shown through the increase of the success rate, the three-biomarker method has a higher separation power between the subjects that have cancer versus those that have other affections, as compared to using TK alone or using the two-biomarker method. Thus, in the group of acutely ill dogs (SIRS), some with sepsis, including CNP, the cases of inflammation associated with sepsis/SIRS yield excellent separation from those with cancer, whereas the inclusion of the inflammatory response (c-CRP) was insufficient in separating the subjects with sepsis.

Alternatively, to further validate the teachings of the invention, the methods described above i.e. TK alone vs. two-biomarker method (TK and CRP) versus three-biomarker method (TK, CRP and CNP), were tested in a group of dogs affected by hemoabdomen affection. The subjects had no documented septic cases. The levels of the three biomarkers was measured, and the data analyzed using ROC method. Table 8 shows the AUC values for each method.

TABLE 8

ROC AUC for TK vs. 2-biomarker vs. 3-biomarker in hemoabdomen dogs

| Status | TK Only | Neoplasia Index (TK&CRP) | Neoplasia Index (TK & CRP & pCNP) |
|---|---|---|---|
| Benign vs. Cancer | .878 | .925 | .937 |

While AUC with TK alone is 0.878 (or 87.8%), the AUC with the two-biomarker method and the three-biomarker method are 0.925 (or 92.5%) and 0.937 (or 93.7%), respectively, indicating that the further inclusion of the third biomarker in the neoplasia index does not dramatically improve the separation power of the ROC analysis, as these dogs are aseptic.

Sepsis Detection in Dogs using CRP and CNP

In accordance with the method of the invention described in FIG. 1, an embodiment of the invention targets the detection of sepsis using two or more biomarkers. To the latter end, a study was conducted on a cohort of thirty six (36) dogs to evaluate a dual biomarker method using CRP and CNP. The group of recruited subjects comprises Dogs with the following diagnosed affections: 7 with cancer, 14 with sepsis and 15 SIRS. c-CRP and c-CNP were measured in each subject.

Figure 12:
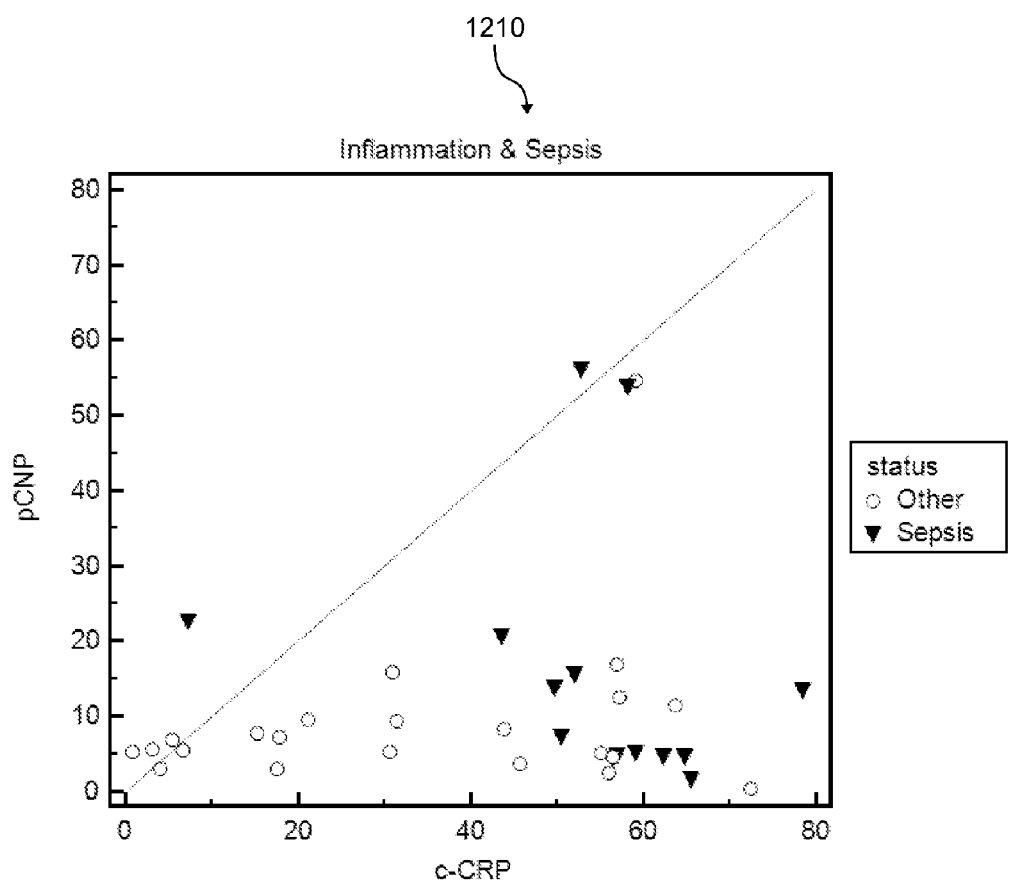
FIG. 12 shows a scatter plot representing c-CNP vs. c-CRP data in a group studied for sepsis.

FIG. 12 shows a scatter plot representing data in a group studied for sepsis. The data points of plot 1210 represent the concentration of CRP (abscissa), the concentration of CNP (ordinate) and whether the subject has sepsis (square) versus other ailments (circle). Plot 1210 visually reveals that the dogs affected by sepsis (as represented by squares) have a relatively high levels of both CNP and CRP, thus pointing out the association between sepsis and inflammation.

Following the teachings of the invention in formula (1), a sepsis index may be computed as follows in formula (4):

$$S_2 = k_2 \cdot dCNP + l_2 \cdot dCRP \qquad (4)$$

Where "$S_2$" denotes the sepsis index in a two-biomarker method using CNP and CRP, and where "$k_2$" and "$l_2$" denote the coefficients associated with CNP and CRP, respectively. CNP and CRP may be represented by concentration (e.g., mass per volume or moles per volume) of blood plasma. "dCRP" and "dCNP" denote the discrete score value matched with a range of CRP level and CNP level, respectively. Table 9 shows the detail of the discretization scores corresponding to ranges for each of CRP and CNP ranges in the two-biomarker method for diagnosing subjects with sepsis.

TABLE 9

Discrete scores for CRP and pCNP ranges

| c-CRP (mg/L) | pCNP (pMole/L) | Score |
|---|---|---|
| 0 to 40.0 | 0 to 3.8 | 0 |
| 40.1 to 56.4 | 3.9 to 13.3 | 1 |
| over 56.5 | 13.4 to 20.0 | 2 |
| | over 20.1 | 3 |

In the latter two-biomarker method the coefficients "$k_2$", and "$l_2$" of formula (4) are given the values 1.17 (coefficient for pCNP) and 1.43 (coefficient for CRP), respectively.

FIG. 13 shows plots of the Receiver Operating Characteristic (ROC) curves Sensitivity vs. one hundred (100) minus Specificity results of using CNP data alone and using the two-biomarker (i.e., CNP and CPR) method while considering subjects with sepsis versus subjects diagnosed with other affections. Plot 1310 shows the ROC curve for CNP alone. The area under the curve is 0.599 (or 59.9%). At criterion level of 12.2 pmol/l, the Sensitivity is 50%, while Specificity is 85.2%.

Plot 1350 shows the ROC curve for the two-biomarker sepsis index (i.e., based on CNP and CRP). The AUC in the latter case is 0.857 (or 85.7%), and at criterion value of greater than 2.86 Sensitivity is 85.7 and Specificity is 86.4. The two-biomarker method has increased the segregation power of the sepsis index between the subjects that have sepsis versus those that have other affections as compared to using CNP alone.

Sepsis Detection in Dogs using CNP, CRP and TK

The sepsis diagnosis study on the cohort of 36 dogs was extended to include TK as a third biomarker in a three-biomarker method. CNP, CRP and TK were measured in the blood serum from each subject.

Figure 14:
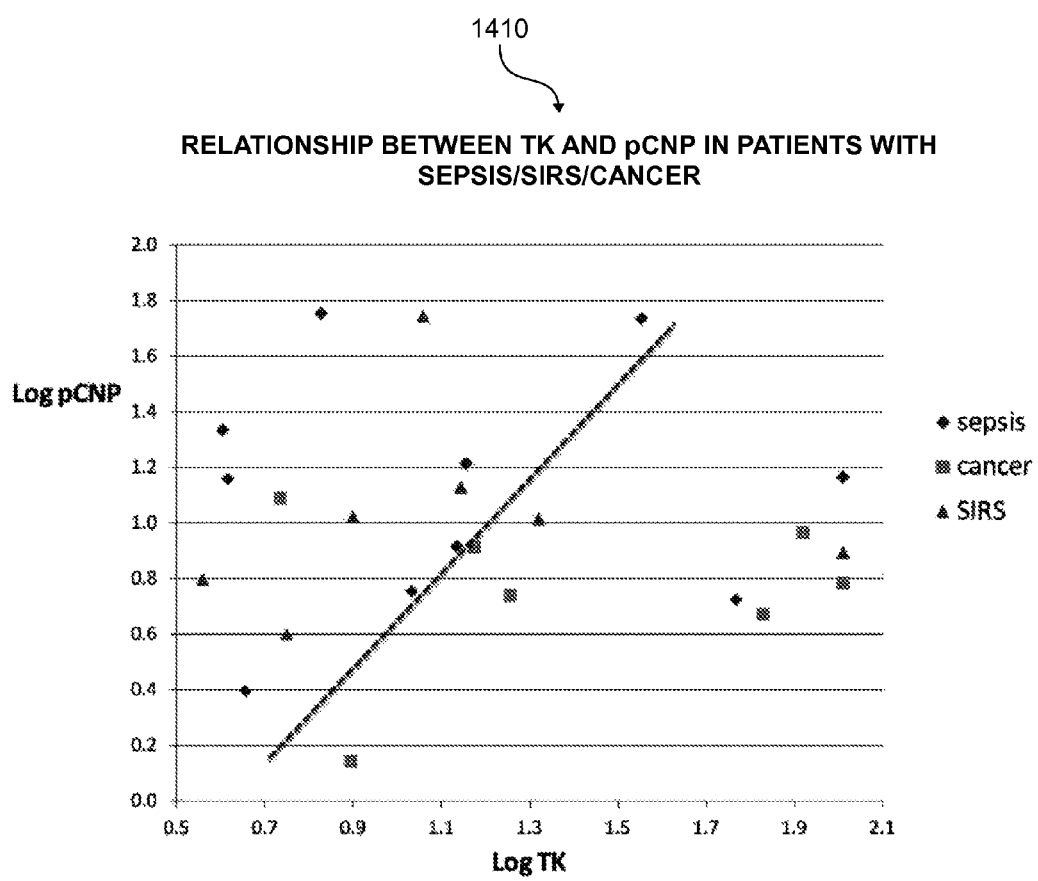
FIG. 14 shows scatter plots representing TK vs. CNP data in a group studied for sepsis, cancer and SIRS.

FIG. 14 shows scatter plots representing data in a group studied for sepsis, cancer and SIRS showing CNP and TK data. The data points of plot 1410 represent the logarithm of level value of TK (abscissa), the logarithm of level value of CNP (ordinate) and whether a subject is affected by sepsis (diamond), cancer (squares) or SIRS (triangle). Plot 1410 visually reveals an overlap of the data from the subjects affected by sepsis, cancer and SIRS.

Following the teachings of the invention in formula (1), a sepsis index may be computed using the three-biomarker method as follows in formula (5):

$$S_3 = k_3 \cdot dCNP + l_3 \cdot dCRP - m_3 \cdot dTK \qquad (5)$$

Where "S3" denotes the sepsis index for three-biomarker method using CNP, CRP and TK; "$k_3$", "$l_3$", and "$m_3$" denote the coefficients associated with CNP, CRP and TK, respectively; and "dCNP", "dCRP" and "dTK" denote the discretized scores of the levels of CNP, CRP and TK, respectively.

Table 10 shows the detail of the discretization scores corresponding to ranges for each of CRP and pCNP and TK in the three-biomarker method for diagnosing subjects with sepsis.

TABLE 10

Discrete scores for CRP, pCNP and TK ranges

| CRP (mg/L) | pCNP (pMole/L) | TK (U/L) | Score |
|---|---|---|---|
| 0 to 40.0 | 0 to 3.8 | 0 to 4.2 | 0 |
| 40.1 to 56.4 | 3.9 to 13.3 | 4.2 to 13.3 | 1 |
| over 56.5 | 13.4 to 20.0 | over 13.4 | 2 |
|  | over 20.1 |  | 3 |

In the latter three-biomarker method for sepsis index, in formula (5), the coefficient "$k_3$" associated with CNP is assigned the value 1.2, the coefficient "$l_3$" associated with CRP is assigned the value 1.47, and the coefficient "$m_3$" is assigned the value 0.27.

The Receiver Operating Characteristic (ROC) analysis shows that the area under the curve is 0.867 (or 86.7%), as compared with the AUC with the two-biomarker method for sepsis (above) the inclusion of the third biomarker (TK) in the sepsis index has increased the separation power of the ROC analysis.

Thus, a method and system for selecting a set of biomarkers and developing a method of use for detecting one or more target diseases and differentiating between the diseases to help a practitioner interpret the test results and potentially reveal the underlying affection or the propensity of a patient to develop a given disease.

The claimed invention is:

1. A method for detecting sepsis in canine subjects comprising the steps of:
   obtaining a blood serum sample from a canine subject;
   obtaining the concentration of c-reactive protein in said blood serum sample and assigning a first discrete value to said c-reactive protein concentration, wherein said first discrete value is assigned a value:
   zero (0) when the concentration of c-reactive protein is less than 40 mg/l,
   one (1) when the concentration of c-reactive protein is between 40.1 mg/l and 56.4 mg/l, or
   two (2) when the concentration of c-reactive protein is greater than 56.5 mg/l;
   obtaining the concentration of C-type natriuretic peptide in said blood serum sample and assigning a second discrete value to said C-type natriuretic peptide concentration, wherein said second discrete value is assigned the value:
   zero (0) when said concentration of C-type natriuretic peptide is less than 3.8 picomole/l,
   one (1) when the concentration of C-type natriuretic peptide is between 3.9 picomole/l and 13.3 picomole/l,
   two (2) when the concentration of C-type natriuretic peptide is between 13.4 picomole/l and 20 picomole/l, or
   three (3) when the concentration of C-type natriuretic peptide is greater than 20.1 picomole/l;
   computing an index value by adding:
   the first discrete value multiplied by a c-reactive protein weighing coefficient of value 1.43, and
   the second discrete value multiplied by a C-type natriuretic peptide weighing coefficient of value 1.17, and
   determining that the canine subject is a carrier of sepsis if said index value is above a criterion value of 2.86.

2. A method for detecting sepsis in canine subjects comprising the steps of:
   obtaining a blood serum sample from a canine subject;
   obtaining the enzymatic level of thymidine kinase in the blood serum sample sample and assigning a first discrete value to said thymidine kinase activity, wherein said first discrete value is assigned a value:
   zero (0) when the level of thymidine kinase activity is less than 4.2 U/I,
   one (1) when the level of thymidine kinase activity is between 4.2 U/I and 13.3 U/I, or
   two (2) when the level of thymidine kinase activity is greater than 13.4 U/I;
   obtaining the concentration of c-reactive protein in said blood serum sample and assigning a second discrete value to said c-reactive protein concentration, wherein said second discrete value is assigned a value:
   zero (0) when the concentration of c-reactive protein is less than 40 mg/l,
   one (1) when the concentration of c-reactive protein is between 40.1 mg/l and 56.4 mg/l, or
   two (2) when the concentration of c-reactive protein is greater than 56.5 mg/l;
   obtaining the concentration of C-type natriuretic peptide in said blood serum sample and assigning a third discrete value to said C-type natriuretic peptide concentration, wherein said third discrete value is assigned the value:
   zero (0) when said concentration of C-type natriuretic peptide is less than 3.8 picomole/l,
   one (1) when the concentration of C-type natriuretic peptide is between 3.9 picomole/l and 13.3 picomole/l,
   two (2) when the concentration of C-type natriuretic peptide is between 13.4 picomole/l and 20 picomole/l, or
   three (3) when the concentration of C-type natriuretic peptide is greater than 20.1 picomole/l;
   computing an index value by adding:
   the first discrete value multiplied by a thymidine kinase weighing coefficient of value 0.27,
   the second discrete value multiplied by a c-reactive protein weighing coefficient of value 1.47, and
   the third discrete value multiplied by a C-type natriuretic peptide weighing coefficient of value 1, and
   determining that the canine subject is a carrier of sepsis if said index value is above a criterion value of 2.94.

* * * * *